United States Patent
Ohta et al.

(10) Patent No.: US 9,322,931 B2
(45) Date of Patent: Apr. 26, 2016

(54) RADIATION IMAGING SYSTEM

(71) Applicant: FUJIFILM Corporation, Tokyo (JP)

(72) Inventors: Yasunori Ohta, Ashigarakami-gun (JP); Haruyasu Nakatsugawa, Ashigarakami-gun (JP); Naoyuki Nishino, Ashigarakami-gun (JP); Naoto Iwakiri, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 196 days.

(21) Appl. No.: 14/107,972

(22) Filed: Dec. 16, 2013

(65) Prior Publication Data

US 2014/0103222 A1 Apr. 17, 2014

Related U.S. Application Data

(63) Continuation of application No. PCT/JP2012/066529, filed on Jun. 28, 2012.

(30) Foreign Application Priority Data

Jun. 30, 2011 (JP) .................................. 2011-146653

(51) Int. Cl.
*G01J 1/42* (2006.01)
*G01T 1/17* (2006.01)
*G01T 1/20* (2006.01)
(Continued)

(52) U.S. Cl.
CPC . *G01T 1/17* (2013.01); *A61B 6/025* (2013.01); *A61B 6/4283* (2013.01); *A61B 6/4452* (2013.01); *G01T 1/2014* (2013.01); *A61B 6/0407* (2013.01); *A61B 6/4233* (2013.01)

(58) Field of Classification Search
CPC ....... H04N 5/357; H04N 5/361; H04N 5/367; H04N 5/2176; H04N 5/32; H04N 5/3651; H04N 5/3415; H04N 5/349; H04N 5/3597
See application file for complete search history.

(56) References Cited

U.S. PATENT DOCUMENTS 8,817,947 B2 * 8/2014 Vedantham et al. ............ 378/21
2003/0043959 A1 3/2003 Wischmann et al.
(Continued)

FOREIGN PATENT DOCUMENTS

JP 2003-107163 A 4/2003
JP 2006-263452 A 10/2006
(Continued)

OTHER PUBLICATIONS

International Search Report, mailed Aug. 7, 2012, issued in PCT/JP2012/066529.
(Continued)

*Primary Examiner* — Mark R Gaworecki
*Assistant Examiner* — Kenneth J Malkowski
(74) *Attorney, Agent, or Firm* — Birch, Stewart, Kolasch & Birch, LLP

(57) ABSTRACT

This radiation imaging system has a radiation source, a case, and a radiation detection device which is housed in the case, and is equipped with a radiation detector having a conversion unit that converts radiation from the radiation source, which has passed through at least a subject, to radiation image information, wherein a prediction is made as to whether the afterimage phenomenon has occurred in the conversion unit, and if it is predicted that the phenomenon has occurred, at least the conversion unit is moved.

17 Claims, 16 Drawing Sheets

(51) Int. Cl.
*A61B 6/02* (2006.01)
*A61B 6/00* (2006.01)
*A61B 6/04* (2006.01)

(56) References Cited

U.S. PATENT DOCUMENTS

| | | |
|---|---|---|
| 2005/0111616 A1* | 5/2005 | Li et al. .......................... 378/22 |
| 2006/0180768 A1 | 8/2006 | Bogdanovich et al. |
| 2006/0180771 A1 | 8/2006 | Jing et al. |
| 2006/0192131 A1 | 8/2006 | Cheung et al. |
| 2009/0060138 A1 | 3/2009 | Van De Haar |
| 2010/0006767 A1 | 1/2010 | Enomoto |
| 2010/0051816 A1 | 3/2010 | Snoeren et al. |
| 2010/0091945 A1* | 4/2010 | Kotani ............................ 378/62 |
| 2010/0124312 A1* | 5/2010 | Enomoto et al. ................ 378/21 |
| 2011/0317054 A1* | 12/2011 | Kameshima et al. ......... 348/302 |

FOREIGN PATENT DOCUMENTS

| | | |
|---|---|---|
| JP | 2007-199065 A | 8/2007 |
| JP | 2007-296337 A | 11/2007 |
| JP | 2009-514636 A | 4/2009 |
| JP | 2009-254660 A | 11/2009 |
| JP | 2010-17376 A | 1/2010 |
| JP | 2010-523997 A | 7/2010 |

OTHER PUBLICATIONS

Written Opinion of the International Search Report, mailed Aug. 7, 2012, issued in PCT/JP2012/066529.

Japanese Office Action, dated Jun. 23, 2015, for Japanese Application No. 2013-522937, with an English translation.

* cited by examiner

FIG. 12A  PRESENT COORDINATE INFORMATION TABLE
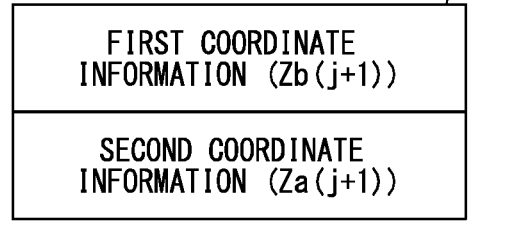
FIG. 12B  PRECEDING COORDINATE INFORMATION TABLE
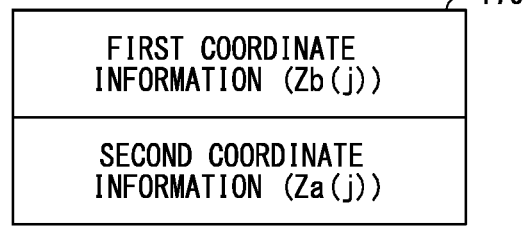
FIG. 12C  MOVEMENT INFORMATION TABLE
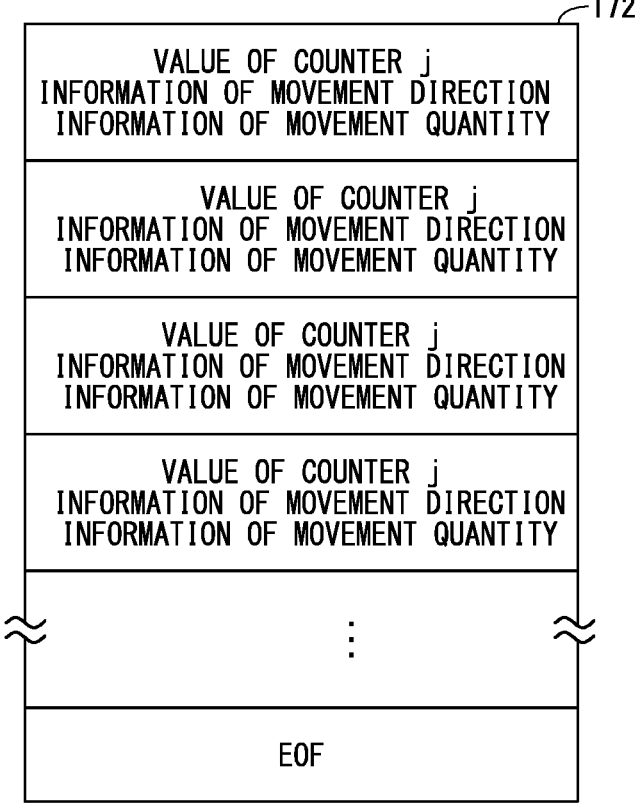

RADIATION IMAGING SYSTEM

CROSS-REFERENCE TO RELATED APPLICATIONS AND PRIORITY CLAIM

This application is a Continuation of International Application No. PCT/JP2012/066529 filed on Jun. 28, 2012, which was published under PCT Article 21(2) in Japanese, which is based upon and claims the benefit of priority from Japanese Patent Application No. 2011-146653 filed on Jun. 30, 2011, the contents all of which are incorporated herein by reference.

TECHNICAL FIELD

The present invention relates to a radiographic image capturing system having a radiation detecting device for converting radiation from a radiation source that has passed through a subject into radiographic image information. More particularly, the present invention relates to a radiographic image capturing system suitable for carrying out a tomosynthetic image capturing process to acquire a tomographic image according to radiography.

BACKGROUND ART

In the medical field, portable radiographic image capturing apparatus such as an FPD (Flat Panel Detector) have been used for detecting the intensity of radiation that has passed through a human body in order to capture an image of the inside of the human body. An FPD (hereinafter referred to as an "electronic cassette") can be used flexibly on patients who cannot move, because the electronic cassette is capable of capturing images of a patient lying on a bed or the like, and can be changed in position in order to adjust the areas to be imaged.

Electronic cassettes include an indirect-conversion-type electronic cassette having a scintillator for temporarily converting radiation into visible light, and a solid-state detector for converting visible light into electric signals. In particular, an electronic cassette including a scintillator made of CsI (cesium iodide) has a high response speed and a high detection capability, and hence is of high performance.

However, an electronic cassette having a scintillator made of CsI tends to suffer from a so-called bright-burn phenomenon, which is a type of afterimage, as a phenomenon unique to CsI scintillators. Bright-burn phenomena occur especially if the scintillator is irradiated with intense radiation. According to a radiographic image capturing process, the electronic cassette captures an image with radiation at an increased dose, and thereafter, an image is captured again with radiation. If the electronic cassette captures an image with radiation at an increased dose, many traps are developed unevenly in the scintillator. If an image is captured again with radiation using the electronic cassette, information represented by the traps is added as radiographic image information and is output from the scintillator. The scintillator tends to bring about irregular sensitivity rises due to bright-burn phenomena, which result in a reduction in contrast and hence a drop in image quality. These problems lead to a reduction in accuracy if subjects are diagnosed by interpreting the captured image.

Heretofore, methods have been proposed for minimizing bright-burn phenomena, as disclosed in Japanese Laid-Open Patent Publication No. 2003-107163, Japanese Laid-Open Patent Publication No. 2010-523997, and Japanese Laid-Open Patent Publication No. 2009-514636.

According to Japanese Laid-Open Patent Publication No. 2003-107163, the scintillator is heated to discharge electric charges held by deep traps.

According to Japanese Laid-Open Patent Publication No. 2010-523997, after a radiographic image has been captured, ultraviolet radiation is applied to the scintillator from a side opposite to an X-ray-irradiated surface thereof, thereby causing the scintillator to emit light, and image information generated by the emitted light is used to perform a correction (calibration).

According to Japanese Laid-Open Patent Publication No. 2009-514636, a main image capturing process is preceded by application of radiation to the scintillator in order to form deep traps in the scintillator over the entirety thereof, thereby holding local sensitivity rises to a minimum.

The bright-burn phenomenon is generally referred to as an afterimage phenomenon. Afterimage phenomena also occur in direct-conversion-type electronic cassettes made of selenium, and are referred to as "ghost" phenomena. Similar to the case of bright-burn phenomena, ghost phenomena occur due to electric charges, which remain in selenium from a preceding image capturing process, and are added and output as radiographic image information in a subsequent image capturing process. Thus, the scintillator tends to bring about irregular sensitivity rises due to such ghost phenomena, which leads to a reduction in contrast and hence a drop in image quality.

Heretofore, an attempt has been made to reduce the occurrence of ghost phenomena with an upper electrode, which is disposed directly in physical and electric contact with an electric charge generator layer that includes a base made of amorphous selenium (see Japanese Laid-Open Patent Publication No. 2006-263452). According to another prior art example, an upper electrode is disposed over an electric charge generator layer, which includes a base made of amorphous selenium with a non-insulating organic layer interposed therebetween, thus making it possible to transport electric charges across the non-insulating organic layer in order to reduce the occurrence of ghost phenomena (see Japanese Laid-Open Patent Publication No. 2007-199065 and Japanese Laid-Open Patent Publication No. 2007-296337). Since there is no electric charge barrier layer, thin-film transistors, which are coupled with signal storage capacitors, are likely to experience break down upon exposure to intensive radiation. However, a structure for positively passing a leakage current is employed in order to prevent the thin-film transistors from breaking down.

SUMMARY OF INVENTION

The method disclosed in Japanese Laid-Open Patent Publication No. 2003-107163 is problematic in that, since the scintillator needs to be heated, a certain period of time is required after an image is captured until the scintillator can be heated to discharge electric charges held by deep traps. Hence, the disclosed method is not applicable to an image capturing process for capturing successive images in a short period of time.

The method disclosed in Japanese Laid-Open Patent Publication No. 2010-523997, which obtains a corrective image in advance by applying ultraviolet radiation to the scintillator from a side opposite to the X-ray-irradiated surface, may not necessarily be capable of generating an accurate corrective image, since the amount of light emitted from the scintillator upon exposure to ultraviolet radiation is small. Another problem is that, inasmuch as the casing and internal structural members of the electronic cassette must be made of a material that is permeable to ultraviolet radiation, the degree of freedom in designing the electronic cassette is low, which poses a limitation on efforts to reduce the cost of the electronic cassette.

The method disclosed in Japanese Laid-Open Patent Publication No. 2009-514636 is disadvantageous in that, since bright-burn is a phenomenon that lasts a few days, it is doubtful that the electronic cassette can be controlled after bright-burning thereof has been caused intentionally.

The approaches disclosed in Japanese Laid-Open Patent Publication No. 2006-263452, Japanese Laid-Open Patent Publication No. 2007-199065, and Japanese Laid-Open Patent Publication No. 2007-296337 are problematic in that, since the upper electrode must be made of a material that has a lower work function than the electric charge generator layer disposed beneath the upper electrode, and which is chemically stable if placed in contact with selenium, the electronic cassette is designed with a low degree of freedom, which poses a limitation on efforts to reduce the cost of the electronic cassette. In addition, the operation timings and circuit arrangements thereof need to be reconfigured in order to prevent a leakage current, which is passed positively upon exposure to strong radiation, from adversely affecting gate drivers and output circuits. Consequently, the circuit arrangements are likely to be complicated and highly costly.

The present invention has been made in view of the aforementioned drawbacks. It is an object of the present invention to provide a radiographic image capturing system, which is simple in structure and capable of capturing radiographic images while staying clear of areas where afterimage phenomena (bright-burn or ghost phenomena) tend to occur, thereby preventing the S/N ratio and contrast from being lowered, and which is reduced in cost without lowering the degree of freedom in designing the radiation detecting device.

[1] A radiographic image capturing system according to a first aspect of the invention comprises a radiation source and a radiation detecting device including a casing and a radiation detector housed in the casing, the radiation detector having a converter for converting radiation emitted from the radiation source and that has passed through at least a subject into radiographic image information, wherein it is predicted whether or not an afterimage phenomenon will occur in the converter, and if it is predicted that an afterimage phenomenon will occur in the converter, at least the converter is moved.

The afterimage phenomenon may refer to a bright-burn phenomenon if the radiation detecting device is of an indirect conversion type comprising a scintillator made of CsI (cesium iodide), for example. Alternatively, the afterimage phenomenon may refer to a ghost phenomenon if the radiation detecting device is of a direct conversion type, which is made of selenium (Se).

[2] In the first aspect of the invention, the radiographic image capturing system may further comprise a controller for controlling at least the radiation source and the radiation detecting device, wherein the controller moves at least the converter if it is predicted that the afterimage phenomenon will occur.

[3] A radiographic image capturing system according to a second aspect of the invention comprises a radiation source, a radiation detecting device including a casing and a radiation detector housed in the casing, the radiation detector having a converter for converting radiation emitted from the radiation source that has passed through at least a subject into radiographic image information, a moving unit for moving at least the converter, a timing prediction unit for predicting a target timing at which to irradiate an area, which has been irradiated with radiation that has not passed through the subject in a preceding radiographic image capturing process, with radiation that passes through the subject in a next radiographic image capturing process, and a controller, wherein the controller controls the moving unit to move at least the converter prior to a radiographic image capturing process carried out at the predicted target timing.

[4] In the second aspect of the invention, a first direction may be defined as a direction along an irradiated surface of the radiation detecting device, and a second direction may be defined as a direction normal to the irradiated surface of the radiation detecting device, and the moving unit may translate at least the converter in the first direction.

[5] In the second aspect of the invention, the moving unit may rotate at least the converter about the second direction.

[6] In the second aspect of the invention, the moving unit may translate at least the converter in the first direction and rotate at least the converter about the second direction.

[7] In the second aspect of the invention, the moving unit may move the radiation detecting device.

[8] In the second aspect of the invention, the moving unit may move only the converter in the radiation detecting device.

[9] In the second aspect of the invention, the radiographic image capturing system may further comprise a second moving unit for moving the radiation source, which is disposed in confronting relation to the radiation detecting device, to a plurality of positions, wherein the controller may control the radiation source at the positions to apply radiation in different directions to the subject over the radiation detecting device.

[10] The second moving unit may move only the radiation source.

[11] Alternatively, the second moving unit may move the radiation source and the radiation detecting device synchronously in opposite directions while the subject is disposed between the radiation source and the radiation detecting device.

[12] In the second aspect of the invention, the timing prediction unit may predict the target timing at which to irradiate the area, which has been irradiated with the radiation that has not passed through the subject in the preceding radiographic image capturing process, with the radiation that passes through the subject in the next radiographic image capturing process at the positions.

[13] The timing prediction unit may predict the target timing based on a simulation of the radiographic image capturing processes at the positions.

[14] Alternatively, the timing prediction unit may predict the target timing based on history information of the radiographic image capturing processes at the positions.

[15] Further, alternatively, the timing prediction unit may predict the target timing each time that the radiation source reaches one of the positions.

[16] In the present invention, the timing prediction unit may comprise a first coordinate acquiring unit for acquiring first coordinate information representing the area that is irradiated with the radiation that has not passed through the subject in the preceding radiographic image capturing process, a second coordinate acquiring unit for acquiring second coordinate information representing an area that is irradiated with the radiation that passes through the subject in the next radiographic image capturing process, and a timing information output unit for sending a timing for carrying out the next radiographic image capturing process as the target timing to the controller, if the area represented by the first coordinate information and at least a portion of the area represented by the second coordinate information overlap with each other, wherein the controller may actuate the moving unit prior to a radiographic image capturing process to be carried out at the predicted target timing, so as to move at least the converter in a direction to reduce the portion of the area represented by the second coordinate information that overlaps with the area represented by the first coordinate information.

[17] One radiographic image capturing process may comprise a provisional image capturing process and a main image capturing process subsequent thereto, the first coordinate acquiring unit may acquire the first coordinate information representing the area that is irradiated with the radiation that has not passed through the subject, which is represented by radiographic image information obtained by a preceding provisional image capturing process, and the second coordinate acquiring unit may acquire the second coordinate information representing the area that is irradiated with the radiation that passes through the subject, which is represented by radiographic image information obtained by a next provisional image capturing process.

[18] Alternatively, the radiographic image capturing system may comprise a light-emitting device for emitting light toward the subject prior to each of the radiographic image capturing processes, and a plurality of photodetectors disposed behind the subject, for detecting the light emitted from the light-emitting device, wherein the first coordinate acquiring unit identifies an area that is irradiated with the radiation that has not passed through the subject, based on detected signals obtained from the photodetectors prior to a preceding radiographic image capturing process, and acquires the identified area as the first coordinate information, and the second coordinate acquiring unit may identify an area that is irradiated with the radiation that passes through the subject, based on detected signals obtained from the photodetectors prior to a next radiographic image capturing process, and acquire the identified area as the second coordinate information.

[19] In the present invention, the radiographic image capturing system may further comprise an image correction unit for correcting the radiographic image information obtained by the radiographic image capturing process carried out at the target timing, based on information concerning movement of at least the converter performed by the moving unit.

The radiographic image capturing system according to the present invention predicts a timing at which an afterimage phenomenon (a bright-burn or a ghost phenomenon) will occur prior to a radiographic image capturing process, and moves at least the converter at the predicted timing. Therefore, it is possible to capture an image while avoiding a region in which afterimage phenomena tend to occur. In other words, with a simple arrangement and independently of the outer profile of the subject, it is possible to capture an image while avoiding a region where afterimage phenomena may occur. The radiographic image capturing system further is capable of preventing the S/N ratio and contrast from being lowered, and the cost thereof can be reduced without lowering the degree of freedom in designing the radiation detecting device. According to the present invention, furthermore, the radiographic image capturing system can easily be applied to a tomosynthetic image capturing process, for example, for capturing ten to several tens of radiographic images within a short period of time, thereby enabling an increase in the image quality of a reconstructed tomographic image of the subject.

BRIEF DESCRIPTION OF DRAWINGS

FIG. 12A is a diagram showing the content of a present coordinate information table;

FIG. 12B is a diagram showing the content of a preceding coordinate information table;

FIG. 12C is a diagram showing the content of a movement information table;

DESCRIPTION OF EMBODIMENTS

A radiographic image capturing system according to an embodiment of the present invention, which is applied to carry out a tomosynthetic image capturing process, will be described below with reference to FIGS. 1 through 16.

Figure 1:
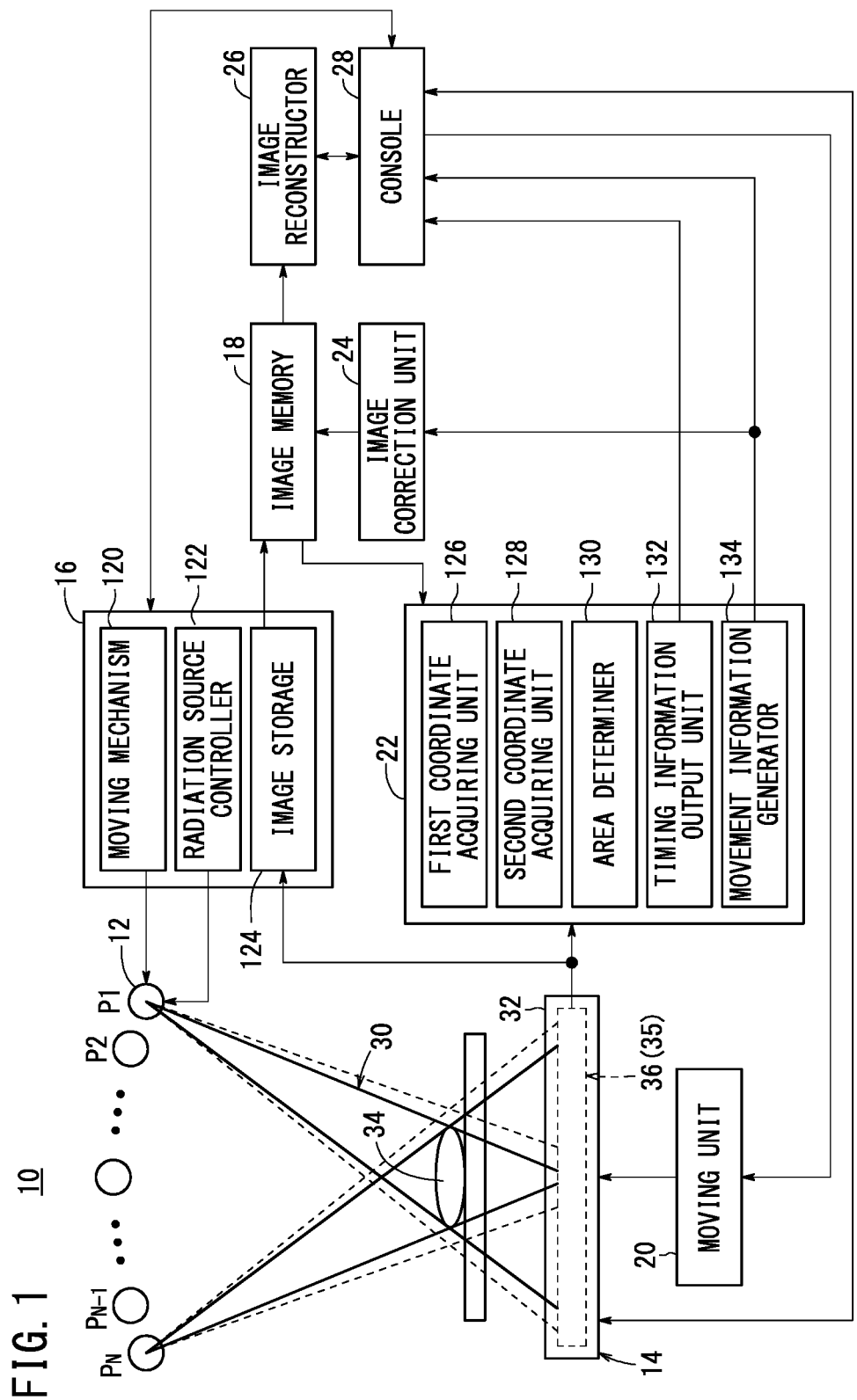
FIG. 1 is a diagram of a radiographic image capturing system according to an embodiment of the present invention.

As shown in FIG. 1, the radiographic image capturing system 10 according to the present embodiment includes a radiation source 12, a radiation detecting device 14, a radiographic image acquiring unit 16, an image memory 18, a moving unit 20, a timing prediction unit 22, an image correction unit 24, an image reconstructor 26, and a console 28 (controller) for controlling the aforementioned components.

The radiation detecting device 14 includes a casing 32 made of a material that is permeable to radiation 30 emitted from the radiation source 12, and a radiation detector 36 (see FIG. 2) having a converter 35 for converting radiation 30 from the radiation source 12 that has passed at least through a subject 34.

Figure 2:
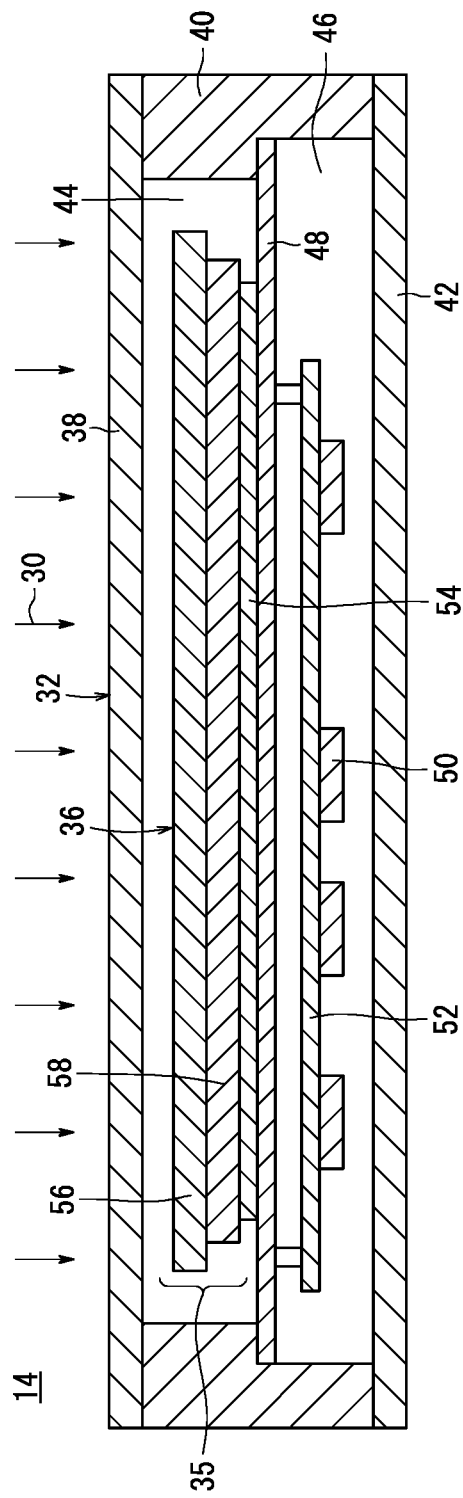
FIG. 2 is a vertical cross-sectional view of a radiation detecting device.

As shown in FIG. 2, the casing 32 has a substantially flat front plate 38 providing a front surface (irradiation surface) that is irradiated with radiation 30, a frame 40 providing side surfaces, a substantially flat rear plate 42 providing a rear surface, and a substantially flat partition 48 disposed in the frame 40, which divides the housing space in the casing 32 into a first compartment 44 near the front plate 38 and a second compartment 46 near the rear plate 42. At least one circuit board 52 with various electronic components 50 mounted thereon is disposed on a rear surface of the partition 48.

The radiation detector 36 is disposed in the first compartment 44, which is surrounded by the front plate 38, the frame 40, and the partition 48. The radiation detector 36 is fixed to the partition 48 by a support plate 54.

The converter 35 of the radiation detector 36 is a surface reading type, i.e., an ISS (Irradiation Side Sampling) type of converter, including a photoelectric transducer board 56 providing a front surface of the converter 35, and a scintillator 58 providing a rear surface of the converter 35. The scintillator 58 is made of a phosphor including a base material of GOS ($Gd_2O_2S$:Tb), CsI:Tl, or the like for converting radiation 30 that has passed through the subject 34 into visible light. The photoelectric transducer board 56 comprises an array of thin-film transistors (TFTs) 60 (see FIG. 3), and a photoelectric conversion layer 64 having solid-state detecting elements 62 (see FIG. 3, hereinafter also referred to as "pixels 62") made of a material such as amorphous silicon (a-Si) for converting visible light into electric signals, the photoelectric conversion layer 64 being disposed on the array of TFTs 60. In other words, the converter 35 comprises the scintillator 58, which functions as a radiation to visible light converter, and the photoelectric conversion layer 64, which functions as a visible light to electric signal converter.

Since, in the ISS-type converter 35, radiation 30 passes through the photoelectric transducer board 56 to the scintillator 58, the photoelectric transducer board 56 must prevent absorption of radiation 30 as much as possible.

The photoelectric transducer board 56 is constructed of an insulating substrate, not shown, the TFTs 60, and the photoelectric conversion layer 64, which are stacked successively along a direction in which radiation 30 is applied. The photoelectric conversion layer 64, which is positioned near the scintillator 58, absorbs electromagnetic waves, e.g., visible light, emitted from the scintillator 58, and generates electric charges depending on the absorbed visible light. More specifically, the photoelectric conversion layer 64 preferably includes a photoelectric conversion film made of a-Si, or an organic photoconductor (OPC) material, or the like. The TFTs 60, which read electric charges generated by the photoelectric conversion layer 64, preferably include an active layer of a-Si, an amorphous oxide, an organic semiconductor material, carbon nanotubes, or the like. The photoelectric transducer board 56, which includes the aforementioned materials, can be fabricated according to a low-temperature process, so as to be flexible and minimize absorption of radiation 30.

The scintillator 58 is fabricated by forming columnar crystals of CsI along a direction in which radiation 30 is applied on an evaporated substrate, not shown, disposed on the surface of the photoelectric transducer board 56, which faces toward the rear surface of the casing 32. If the scintillator 58 is made of columnar crystals of thallium-added cesium iodide (CsI:Tl), and the photoelectric conversion layer 64 is made of quinacridone as an OPC, then the difference between the peak wavelength of light emitted by the scintillator 58 and the peak wavelength of light absorbed by the photoelectric conversion film can be reduced to 5 nm or smaller, for thereby maximizing the amount of electric charges generated by the photoelectric conversion layer 64. The evaporated substrate may comprise a thin aluminum (Al) substrate, which is highly resistant to heat and low in cost.

The material of the scintillator 58 is not limited to CsI or CsI:Tl, but may be CsI:Na (sodium-activated cesium iodide), GOS (gadolinium oxide sulfur, $Gd_2O_2S$:Tb), or the like. According to the present embodiment, the converter 35 may be of the reverse side reading type, i.e., a PSS (Penetration Side Sampling) type, in which the scintillator 58 and the photoelectric transducer board 56 are disposed successively along the direction in which radiation 30 is applied. Alternatively, the converter 35 may be of the direct conversion type for directly converting radiation 30 into electric signals with a plurality of pixels made of amorphous selenium (a-Se) or the like.

Figure 3:
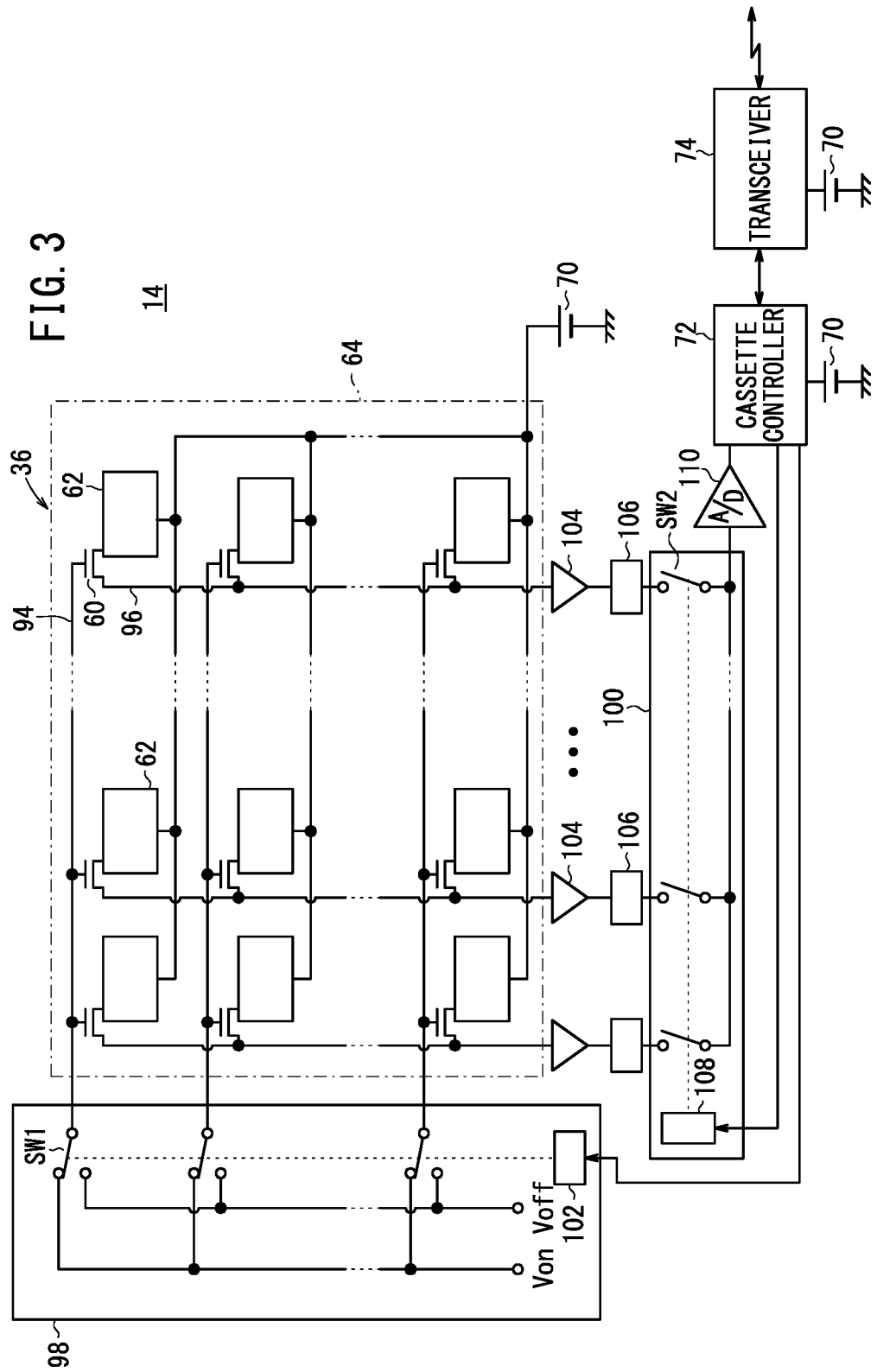
FIG. 3 is a circuit diagram of a circuit arrangement of the radiation detecting device.

The radiation detector 36 converts radiation 30 that has passed through the subject 34 into radiographic image information, and supplies the radiographic image information as electric signals to the radiographic image acquiring unit 16, the console 28, etc. As shown in FIG. 3, the radiation detecting device 14 includes, in addition to the circuit board 52 and the radiation detector 36, a battery 70, a cassette controller 72, and a transceiver 74, etc. The battery 70 serves as a power supply for the radiation detecting device 14. More specifically, electric power is supplied from the battery 70 to the radiation detector 36, the cassette controller 72, and the transceiver 74. The cassette controller 72 energizes the radiation detector 36 with electric power supplied from the battery 70. The transceiver 74 sends and receives signals, which represent information of the radiation 30 (radiographic image information) detected by the radiation detector 36, to and from the radiographic image acquiring unit 16, the console 28, etc.

A circuit arrangement of the radiation detecting device 14 will be described in detail below with reference to FIGS. 3 and 4.

As shown in FIG. 3, the radiation detecting device 14 includes the photoelectric conversion layer 64 comprising pixels 62 made of a material such as a-Si or the like for converting visible light into electric signals. The photoelectric conversion layer 64 is disposed on the array of TFTs 60, which are arranged in rows and columns. The pixels 62 store electric charges generated by converting visible light into electric signals. The stored electric charges are read as image signals from the pixels 62 by successively turning on the rows of TFTs 60.

The TFTs 60, which are connected to the respective pixels 62, are connected to respective gate lines 94 that extend in parallel with the rows, and to respective signal lines 96 that extend in parallel with the columns. The gate lines 94 are connected to a line scanning driver 98, and the signal lines 96 are connected to a multiplexer 100. The gate lines 94 are supplied with control signals Von, Voff from the line scanning driver 98 for turning on and off the TFTs 60 along the rows. The line scanning driver 98 comprises a plurality of switches SW1 for switching between the gate lines 94, and a first address decoder 102 for outputting a selection signal for selecting one of the switches SW1 at a time. The first address decoder 102 is supplied with an address signal from the cassette controller 72.

The signal lines 96 are supplied with electric charges stored in the pixels 62 through the TFTs 60 arranged in the columns. The electric charges are amplified by amplifiers 104, which are connected to the multiplexer 100 through respective sample and hold circuits 106. The multiplexer 100 comprises a plurality of switches SW2 for successively switching between the signal lines 96, and a second address decoder 108 for outputting a selection signal for selecting one of the switches SW2 at a time. The second address decoder 108 is supplied with an address signal from the cassette controller 72. The multiplexer 100 is connected to an A/D converter 110. Radiographic image information, which is converted into digital signals by the A/D converter 110, is supplied to the cassette controller 72.

As shown in FIG. 3, the line scanning driver 98, the multiplexer 100, the amplifiers 104, the sample and hold circuits 106, and the A/D converter 110 are included in the electronic components 50 (see FIG. 2). Portions of the gate lines 94, which extend from the line scanning driver 98 to the photoelectric conversion layer 64, and portions of the signal lines 96, which extend from the photoelectric conversion layer 64 to the amplifiers 104, are included in the photoelectric transducer board 56 (see FIG. 2).

The TFTs 60, which function as switching elements, may be combined with any of various other image capturing devices such as a CMOS (Complementary Metal-Oxide Semiconductor) image sensor, or may be replaced with a CCD (Charge-Coupled Device) image sensor, in which electric charges are shifted and transferred by shift pulses that correspond to gate signals used in the TFTs.

Figure 4:
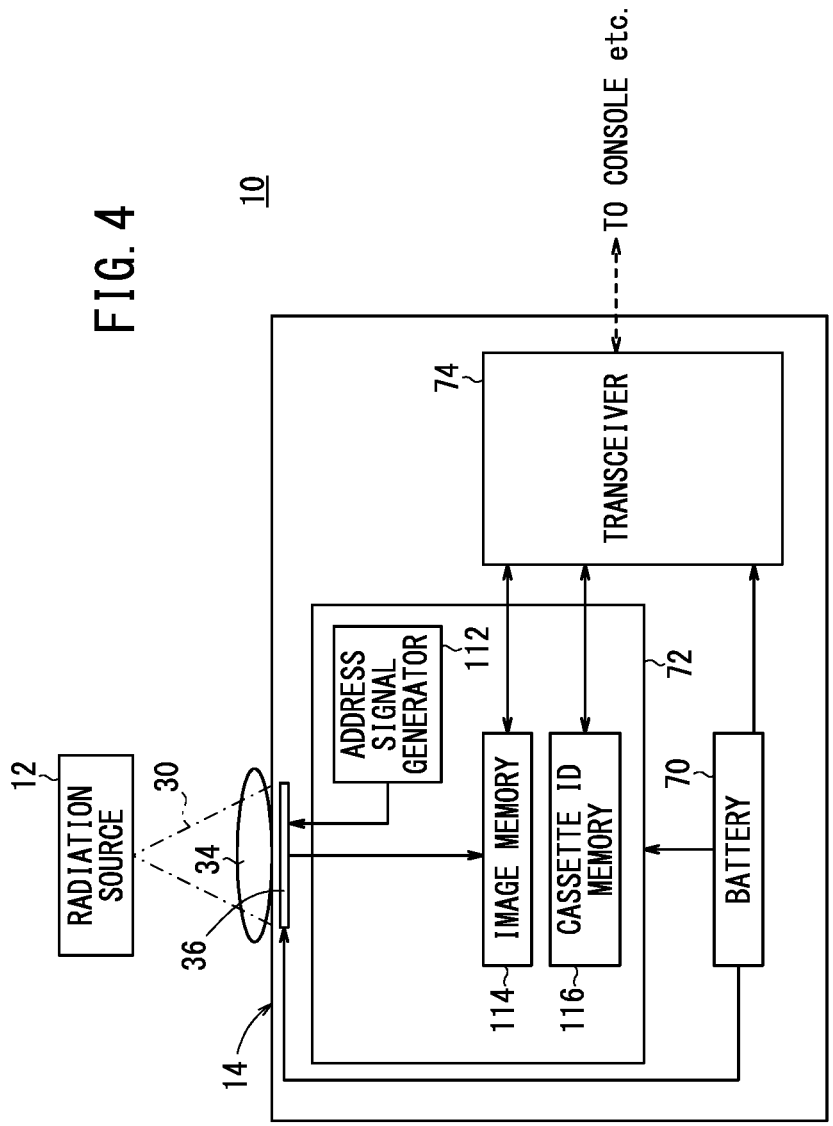
FIG. 4 is a block diagram of the radiation detecting device.

As shown in FIG. 4, the cassette controller 72 of the radiation detecting device 14 includes an address signal generator 112, an image memory 114, and a cassette ID memory 116.

The address signal generator 112 supplies address signals to the first address decoder 102 of the line scanning driver 98, as well as to the second address decoder 108 of the multiplexer 100 shown in FIG. 3. The image memory 114 stores radiographic image information detected by the radiation detector 36. The cassette ID memory 116 stores cassette ID information for identifying the radiation detecting device 14.

The transceiver 74 sends the cassette ID information, which is stored in the cassette ID memory 116, and the radiographic image information, which is stored in the image memory 114, to the radiographic image acquiring unit 16, the console 28, etc.

As shown in FIG. 1, the radiographic image acquiring unit 16 has a moving mechanism 120 (second moving unit) for moving at least the radiation source 12 to a plurality of preset positions $P_1, P_2, \ldots, P_{N-1}, P_N$, a radiation source controller 122 for controlling the radiation source 12 in order to apply radiation 30 to the subject 34 over the radiation detecting device 14 in a case where the radiation source 12 has reached the preset positions $P_1, P_2, \ldots, P_{N-1}, P_N$, and an image storage unit 124 for storing radiographic images in the image memory 18, which are sent successively from the radiation detecting device 14 in chronological order, for example.

Figure 5A:
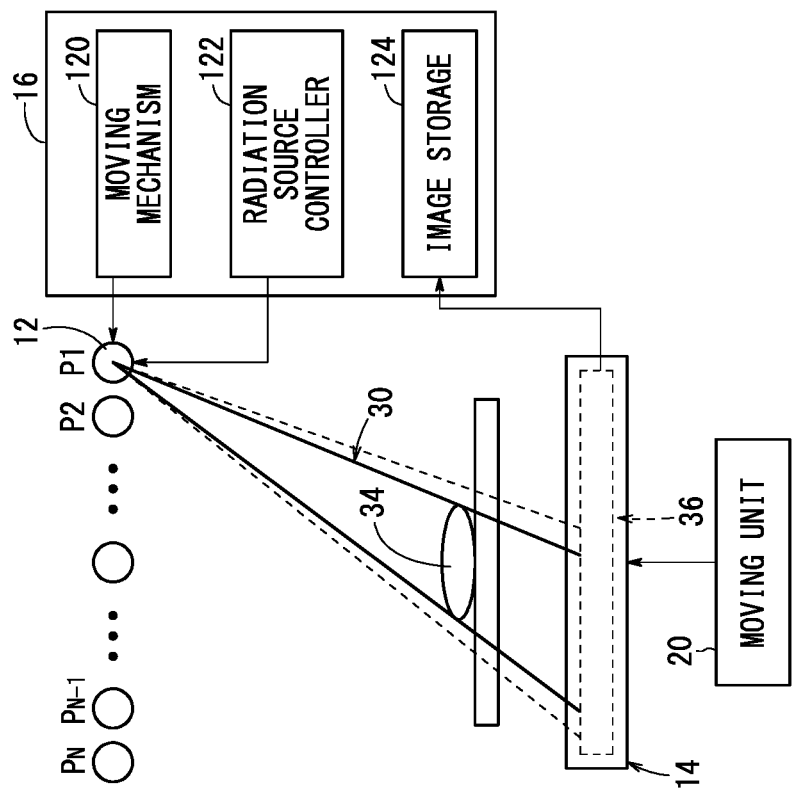
FIG. 5A is a diagram showing a manner in which a radiation source and the radiation detecting device are moved synchronously in opposite directions while a subject is disposed between the radiation source and the radiation detecting device.
Figure 5B:
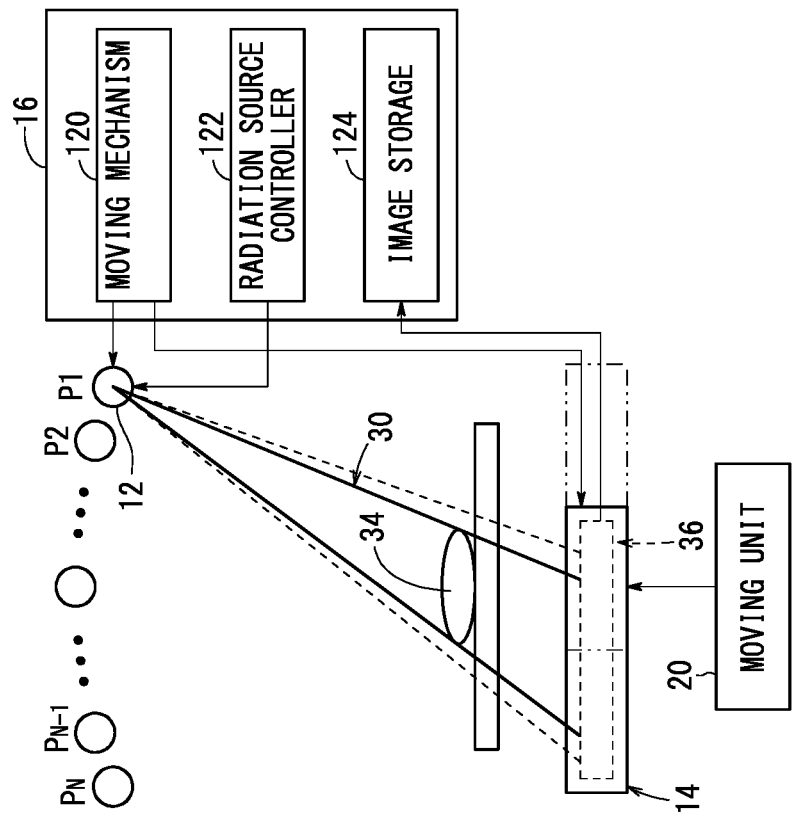
FIG. 5B is a diagram showing a manner in which the radiation source is moved along a straight path.

The radiographic image acquiring unit 16 acquires a plurality of images from the radiation detecting device 14 by moving the radiation source 12, which faces toward the radiation detecting device 14, to the positions $P_1, P_2, \ldots, P_{N-1}, P_N$, and applying radiation 30 in different directions from the radiation source 12 at the respective positions $P_1, P_2, \ldots,$ $P_{N-1}, P_N$ to the subject 34 over the radiation detecting device 14. In FIG. 1, the moving mechanism 120 moves the radiation source 12 essentially along an arcuate path. However, as shown in FIG. 5A, the moving mechanism 120 may move the radiation source 12 and the radiation detecting device 14 synchronously in opposite directions while the subject 34 is disposed between the radiation source 12 and the radiation detecting device 14. Alternatively, as shown in FIG. 5B, the moving mechanism 120 may move the radiation source 12 along a straight path.

The radiographic image acquiring unit 16 captures radiographic images based on two different concepts. One of such concepts is an individual image capturing process, which is carried out in a case where the radiation source 12 has reached each of the positions $P_1, P_2, \ldots, P_{N-1}, P_N$. The other concept is an image capturing process, which collectively represents a plurality of individual image capturing processes. The individual image capturing process will be referred to as a "radiographic image capturing process", whereas the image capturing process that collectively represents a plurality of individual image capturing processes will be referred to as a "tomosynthetic image capturing process".

The moving unit 20 is controlled by the console 28 in order to move the radiation detecting device 14. If the radiation source 12 and the radiation detecting device 14 are moved synchronously by the moving mechanism 120, as shown in FIG. 5A, then the radiation detecting device 14 is moved by the moving mechanism 120 as well as by the moving unit 20.

The timing prediction unit 22 shown in FIG. 1 predicts the timing at which an area of the radiation detecting device 14, which has been irradiated with radiation 30 that has not passed through the subject 34 in a preceding radiographic image capturing process, i.e., an area of the radiation detecting device 14 where an afterimage phenomenon has occurred, will be irradiated with radiation 30 that passes through the subject 34 in a next radiographic image capturing process. The afterimage phenomenon may refer to a bright-burn phenomenon, if the radiation detecting device 14 is of an indirect conversion type having a scintillator made of CsI (cesium iodide), for example. Alternatively, the afterimage phenomenon may refer to a ghost phenomenon, if the radiation detecting device 14 is of a direct conversion type, which is made of selenium (Se).

The timing prediction unit 22 includes a first coordinate acquiring unit 126, a second coordinate acquiring unit 128, an area determiner 130, a timing information output unit 132, and a movement information generator 134.

The first coordinate acquiring unit 126 acquires first coordinate information representing an area of the converter 35 of the radiation detecting device 14, which has been irradiated with radiation 30 that has not passed through the subject 34 in a preceding radiographic image capturing process.

The second coordinate acquiring unit 128 acquires second coordinate information representing an area of the converter 35 of the radiation detecting device 14, which will be irradiated with radiation 30 that passes through the subject 34 in a next radiographic image capturing process.

The area determiner 130 determines whether or not at least a portion of the area represented by the second coordinate information is included within the area represented by the first coordinate information.

The timing information output unit 132 sends to the console 28 information concerning the timing for carrying out a next radiographic image capturing process, as information concerning the predicted timing (hereinafter referred to as a "target timing").

The movement information generator 134 generates information, which is used for moving the radiation detecting device 14 at the target timing.

Information concerning the target timing, which is sent from the timing information output unit 132, may be information indicative of a sequence of radiographic image capturing processes. Accordingly, from among the radiographic image capturing processes carried out respectively at the preset positions, the timing prediction unit 22 predicts a sequence of radiographic image capturing processes such that the area, which has been irradiated with radiation 30 that has not passed through the subject 34 in a preceding radiographic image capturing process, will be irradiated with radiation that passes through the subject 34 in a next radiographic image capturing process. The information, which is indicative of the sequence of radiographic image capturing processes, is supplied to the console 28 as information concerning the target timing.

Several specific methods, which are carried out by the timing prediction unit 22, will be described below.

The first method is a method for predicting a target timing based on a simulation of radiographic image capturing processes performed respectively at the preset positions $P_1$, $P_2$, ..., $P_{N-1}$, $P_N$.

Typically, according to a tomosynthetic image capturing process, an angle formed between a line normal to the irradiated surface of the radiation detecting device 14 and the direction in which radiation 30 is applied, i.e., the direction in which the radiation emitter of the radiation source 12 faces, tends to vary as the radiation source 12 moves. The direction of movement of the radiation source 12, i.e., the sequence in which the radiation source 12 is moved through the preset positions $P_1$, $P_2$, ..., $P_{N-1}$, $P_N$, is determined depending on image capturing conditions. Therefore, if the size (height, weight, etc.) of the subject 34 and an image capturing area of the subject, as well as the movement direction of the radiation source 12 are known, then it is possible to identify the position and size of an area of the radiation detecting device 14, more precisely the converter 35, which is to be irradiated with radiation 30 with respect to the positions $P_1$, $P_2$, ..., $P_{N-1}$, $P_N$ through which the radiation source 12 is moved, i.e., the position and size of an area of the radiation detecting device 14 that is irradiated with radiation 30 that has not passed through the subject 34, as well as to identify the position and size of an area of the radiation detecting device 14 that is irradiated with radiation 30 that has passed through the subject 34.

Figure 6:
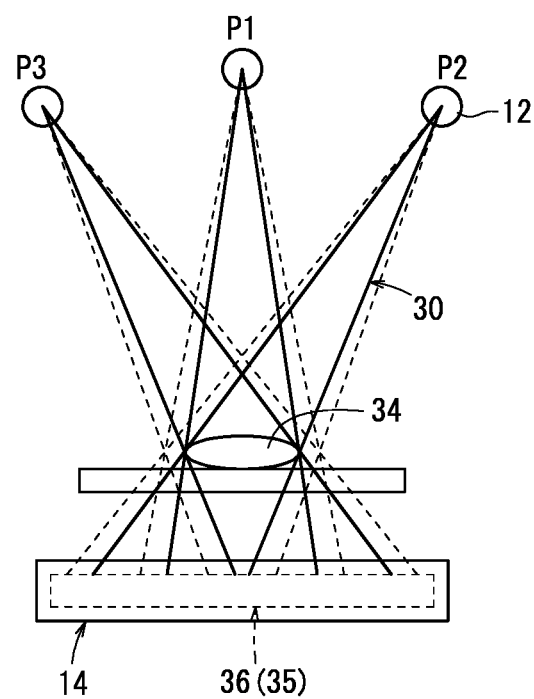
FIG. 6 is a diagram showing a manner in which the radiation source is moved to three positions, and emits radiation toward the subject from each of the positions.
Figure 7:
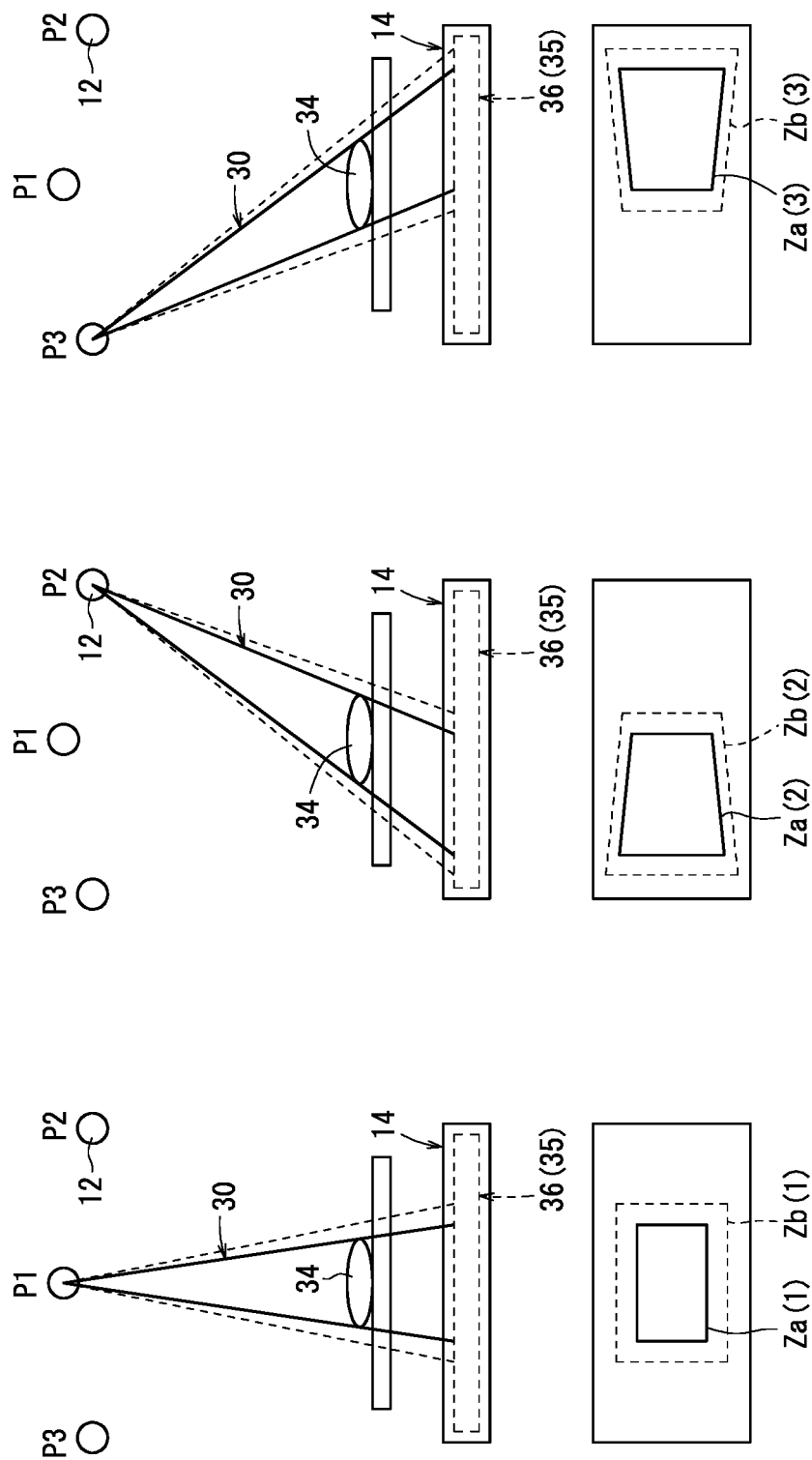
FIGS. 7A through 7C are diagrams showing a manner in which the radiation source is moved to central, left, and right positions, respectively, and emits radiation from such positions toward the subject, while also showing radiation-irradiated areas of the radiation detecting device (converter) at times that radiation is emitted.

The timing (target timing) of a radiographic image capturing process that is affected by an afterimage phenomenon will be described below with reference to FIGS. 6 through 8. In FIGS. 6 through 7C, for the sake of brevity, the radiation source 12 is moved to three positions P1, P2, P3, and emits radiation 30 toward the subject 34 from each of the positions P1, P2, P3. In FIGS. 6 through 7C, the radiation source 12 is moved successively from the position "P1: central" to the position "P2: right" to the position "P3: left". In FIGS. 6 through 7C, furthermore, radiation 30 that passes through the subject 34 is indicated by the solid lines, whereas radiation 30 that does not pass through the subject 34 is indicated by the dotted lines.

As shown in FIG. 7A, if the radiation source 12 is positioned at the position "P1: central" and a radiographic image capturing process is carried out by emitting radiation 30 toward the subject 34 having a rectangular outer profile, a first area Za(1) of the irradiated surface of the radiation detecting device 14, i.e., the irradiated surface of the converter 35, which is irradiated with radiation 30 that has passed through the subject 34, is of a shape similar to and greater than the outer profile of the subject 34, and a second area Zb(1) of the irradiated surface of the radiation detecting device 14, i.e., the irradiated surface of the converter 35, which is irradiated with radiation 30 that has not passed through the subject 34, is of a frame shape that surrounds the first area Za(1) and has an outer profile similar to and greater than the outer profile of the subject 34. Since the second area Zb(1) is positioned remotely from the center of the irradiated surface of the converter 35, the radiation dose emitted from the radiation source 12 and applied to the second area Zb(1) is so small that virtually no afterimage phenomenon occurs in the second area Zb(1).

As shown in FIG. 7B, in a case where the radiation source 12 is positioned at the position "P2: right" and a radiographic image capturing process is carried out, a first area Za(2) of the irradiated surface of the radiation detecting device 14, i.e., the irradiated surface of the converter 35, is of a trapezoidal shape, which is shifted to the left as a whole, and the trapezoidal shape has a left side longer than a right side thereof. In addition, a second area Zb(2) of the irradiated surface of the radiation detecting device 14, i.e., the irradiated surface of the converter 35, is of a frame shape that surrounds the first area Za(2) (trapezoidal shape), and the frame shape has an outer profile similar to the trapezoidal shape of the first area Za(2). Since the shorter size of the second area Zb(2) is positioned substantially at the center of the irradiated surface of the converter 35, the radiation dose emitted from the radiation source 12 and applied to the shorter size of the second area Zb(2) is large, and thus it is highly possible for an afterimage phenomenon to occur in the shorter size of the second area Zb(2).

As shown in FIG. 7C, in a case where the radiation source 12 is positioned at the position "P3: left" and a radiographic image capturing process is carried out, a first area Za(3) of the irradiated surface of the radiation detecting device 14, i.e., the irradiated surface of the converter 35, is of a trapezoidal shape, which is shifted to the right as a whole, and the trapezoidal shape has a right side longer than a left side thereof. In addition, a second area Zb(3) of the irradiated surface of the radiation detecting device 14, i.e., the irradiated surface of the converter 35, is of a frame shape that surrounds the first area Za(3) (trapezoidal shape), and the frame shape has an outer profile similar to the trapezoidal shape of the first area Za(3). Since the shorter size of the second area Zb(3) is positioned substantially at the center of the irradiated surface of the converter 35, the radiation dose emitted from the radiation source 12 and applied to the shorter size of the second area Zb(3) is large, and thus it is highly possible for an afterimage phenomenon to occur in the shorter size of the second area Zb(3).

If the radiographic image capturing process at the position "P2: right" is carried out after the radiographic image capturing process at the position "P1: central", then even though a portion of the first area Za(2) at the position "P2: right" is included within the second area Zb(1) at the position "P1: central", the first area Za(2) remains virtually unaffected by afterimage phenomena.

Figure 8:
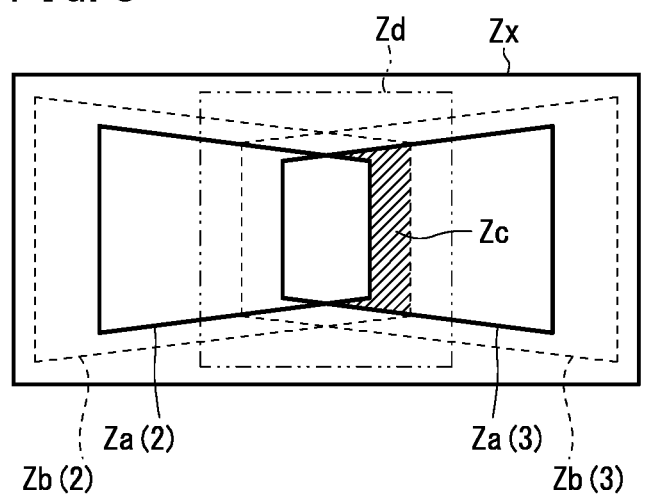
FIG. 8 is a model diagram showing a radiation-irradiated area of the converter at a time that a radiographic image is captured with the radiation source being positioned to the right, and a radiation-irradiated area of the converter at a time that a radiographic image is captured with the radiation source being positioned to the left, such that the radiation-irradiated areas overlap one another.

If the radiographic image capturing process at the position "P3: left" is carried out after the radiographic image capturing process at the position "P2: right", then as shown in FIG. 8, a portion of the first area Za(3) at the position "P3: left" overlaps with the second area Zb(2) at the position "P2: right" (see the portion Zc shown in hatching in FIG. 8). The overlapping portion Zc is included within an area where the dose of radiation 30 is high (i.e., the area Zd indicated by the two-dot-and-dash lines). Therefore, the radiographic image capturing process performed at the position "P3: left" is affected by an afterimage phenomenon developed in the radiographic image capturing process performed at the position "P2: right". In other words, the timing of the radiographic image capturing process performed at the position "P3: left" serves as a target timing, which can be identified by way of simulation.

FIG. 8 is a model diagram showing the radiation-irradiated area of the converter 35, which is irradiated with radiation 30 in the radiographic image capturing process at the position "P2: right", and the radiation-irradiated area of the converter 35, which is irradiated with radiation 30 in the radiographic image capturing process at the position "P3: left", in which the radiation-irradiated areas overlap with each other. Within the entire radiation-irradiated surface of the converter 35, the area Zd, which is irradiated with a higher dose of radiation 30, may be set to a desired shape and size around the center of the entire area Zx (indicated as a greatest rectangle in FIG. 8) of the radiation-irradiated surface of the converter 35. In order to prevent the number of target timings from increasing excessively, the area Zd preferably is set as a square or circular area, the center of which is aligned with the center of the entire area, and the square or circular area has a side or diameter that is set substantially ⅕ to ⅓ of the longer sides of the entire area. Of course, it is possible for the target timing to be set without taking into account the area Zd where the dose of radiation 30 is high.

According to the first method, the first coordinate acquiring unit 126 of the timing prediction unit 22 acquires, by way of simulation, first coordinate information representing an area Zb(j) that is irradiated with radiation 30 that has not passed through the subject 34, based on jth (j is a natural number of 1 or greater) radiographic image information from among the radiographic image information obtained at the positions $P_1$, $P_2$, ..., $P_{N-1}$, $P_N$. The second coordinate acquiring unit 128 acquires second coordinate information representing an area Za(j+1) that is irradiated with radiation 30 that has passed through the subject 34, based on (j+1)th radiographic image information. The timing information output unit 132 sends information concerning the timing of the (j+1)th radiographic image capturing process (radiographic image capturing process in its turn) as information of a predicted target timing to the console 28, if at least a portion of the area Za(j+1) represented by the second coordinate information is included within the area Zb(j) represented by the first coordinate information and, if necessary, that portion is included within the area Zd where the dose of radiation 30 is high. This process is repeated until the final radiographic image capturing process (Nth radiographic image capturing process) is carried out.

The second method is a method for predicting a target timing using a history of radiographic image information recorded in a database or the like. According to various radiographic image capturing processes, including a tomosynthetic image capturing process, it is customary to store radiographic image information as history information in a database. Consequently, for carrying out a present tomosynthetic image capturing process, it is possible to acquire radiographic image information from the history information, for a case that is similar in relation to the image capturing conditions, the size of the subject 34, and the image capturing area thereof.

The first coordinate acquiring unit 126 of the timing prediction unit 22 acquires first coordinate information representing an area Zb(j) that is irradiated with radiation 30 that has not passed through the subject 34, based on jth radiographic image information from among the acquired radiographic image information. The second coordinate acquiring unit 128 acquires second coordinate information representing an area Za(j+1) that is irradiated with radiation 30 that has passed through the subject 34, based on (j+1)th radiographic image information. From among the radiographic image capturing processes performed at the positions $P_1$, $P_2$, ..., $P_{N-1}$, $P_N$, the timing information output unit 132 sends information concerning the timing of the (j+1)th radiographic image capturing process (radiographic image capturing process in its turn) as information of a predicted target timing to the console 28, if at least a portion of the area Za(j+1) represented by the second coordinate information is included within the area Zb(j) represented by the first coordinate information and, if necessary, that portion is included within the area Zd where the dose of radiation 30 is high. The process is repeated until the final radiographic image capturing process (Nth radiographic image capturing process) is carried out.

According to the first and second methods, a plurality of items of radiographic image information, which are obtained by way of simulation, or a plurality of items of radiographic image information, which are acquired from history information, are collectively processed in order to determine the target timing. Alternatively, the target timing may be determined according to a real-time process in an actual tomosynthetic image capturing process. As will be described below, the third and fourth methods are carried out according to a real-time process.

According to the third method, a provisional image capturing process and a subsequent main image capturing process make up an individual radiographic image capturing process. More specifically, two image capturing processes (a provisional image capturing process and a main image capturing process) are carried out at each of the positions $P_1$, $P_2$, ..., $P_{N-1}$, $P_N$. The first coordinate acquiring unit 126 of the timing prediction unit 22 acquires first coordinate information, which represents an area Zb(j) that is irradiated with radiation 30 that has not passed through the subject 34, from among the radiographic image information obtained in the jth provisional image capturing process. In the provisional image capturing process, radiation 30 is applied at a dose which is smaller than in the main image capturing process, in order to reduce the exposure dose applied to the subject 34. An area, the brightness level of which is equal to or higher than a threshold value in the radiographic image information, may be judged as an area that is irradiated with radiation 30 that has not passed through the subject 34. The threshold value may be selected depending on the radiation dose used in the provisional image capturing process. The second coordinate acquiring unit 128 acquires second coordinate information, which represents an area Za(j+1) that is irradiated with radiation 30 that has passed through the subject 34, from among the radiographic image information obtained by a (j+1)th provisional image capturing process. An area of the radiographic image information, which is produced by subtracting an area, the brightness level of which is equal to or higher than a threshold value, from an entire area defined by the profile of an area, the brightness level of which is equal to or higher than a threshold value, may be judged as an area that is irradiated with radiation 30 that has passed through the subject 34. From among the radiographic image capturing processes performed at the positions $P_1$, $P_2$, ..., $P_{N-1}$, $P_N$, the timing information output unit 132 sends information concerning the timing of the (j+1)th radiographic image capturing process (main image capturing process) as information of a predicted target timing to the console 28, if at least a portion of the area Za(j+1) represented by the second coordinate information is included within the area Zb(j) represented by the first coordinate information and, if necessary, that portion is included within the area Zd where the dose of radiation 30 is high.

Figure 9A:
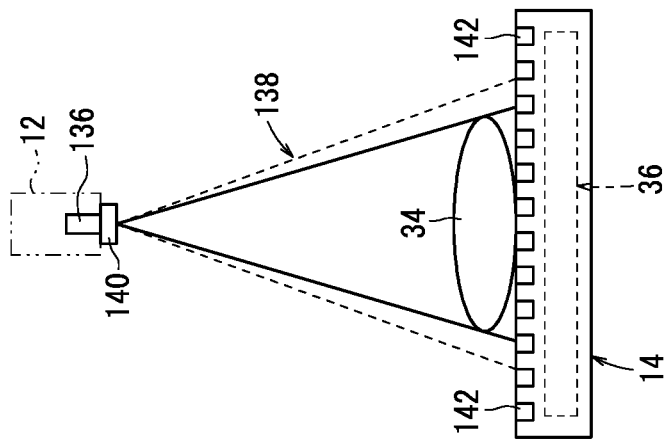
FIG. 9A is a diagram showing a manner in which light emitted from a light-emitting device that is mounted on the radiation source is detected by a plurality of photodetectors that are mounted on an image capturing base.
Figure 9B:
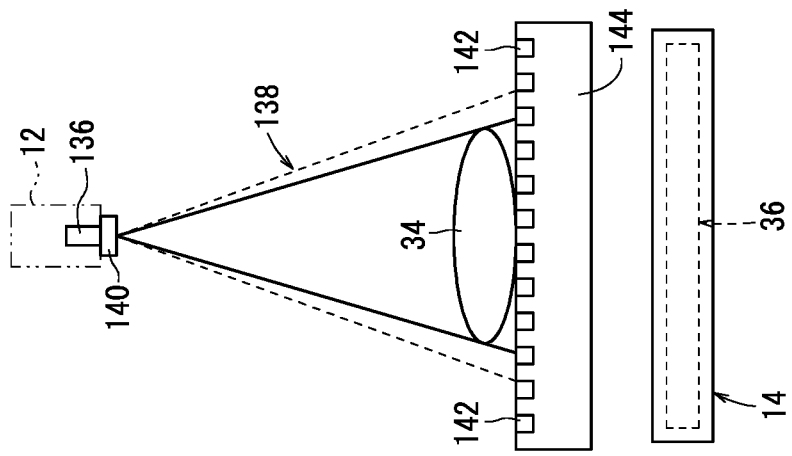
FIG. 9B is a diagram showing a manner in which light emitted from a light-emitting device that is mounted on the radiation source is detected by a plurality of photodetectors that are mounted on the radiation detecting device.

According to the fourth method, instead of the provisional image capturing process carried out in the third method, as shown in FIGS. 9A and 9B, light 138 emitted from a light-emitting device 136 is applied to the subject 34. In FIG. 9A or 9B, light 138 that is applied to the subject 34 is indicated by the solid lines, and light 138 that is not applied to the subject 34 is indicated by the dotted lines.

An area of the surface lying behind the subject 34, which is positioned remotely from the radiation source 12 and concealed by the subject 34, is not irradiated with light 138. Therefore, the first coordinate information and the second coordinate information can be acquired based on the area that is irradiated with light 138 and the area that is not irradiated with light 138.

More specifically, prior to carrying out the radiographic image capturing processes, the light-emitting device 136 for emitting light 138 toward the subject 34 and a collimator 140 are installed on the radiation source 12. A plurality of photodetectors 142, which detect the light 138 that is emitted from the light-emitting device 136, are installed on a surface located behind the subject 34. An aperture of the collimator 140 is set to limit the light 138 emitted from the light-emitting device 136 to substantially the same extent as the radiation 30 emitted from the radiation source 12.

In FIG. 9A, the radiographic image capturing processes are carried out on a subject 34 who is placed on an image capturing base 144. The photodetectors 142, which detect light 138 emitted from the light-emitting device 136, are installed on the irradiated surface of the image capturing base 144. With the photodetectors 142 mounted on the image capturing base 144, since the linear distance from the radiation source 12 to the image capturing base 144 is smaller than the linear distance from the radiation source 12 to the radiation detecting device 14, the area that is irradiated with light 138 and the area that is not irradiated with light 138 are enlarged depending on the difference between the linear distances, whereupon the first coordinate information and the second coordinate information are acquired. In FIG. 9B, the radiation detecting device 14 is installed directly behind the subject 34, and the image capturing base 144 is not interposed between the radiation detecting device 14 and the subject 34. In this case, the photodetectors 142, which detect light 138 emitted from the light-emitting device 136, are mounted on the irradiated surface of the radiation detecting device 14.

In FIGS. 9A and 9B, the photodetectors 142 may be arranged in a matrix, or in a radial pattern at spaced intervals ranging from 0.5 cm to 2 cm.

Prior to a jth radiographic image capturing process, the first coordinate acquiring unit 126 of the timing prediction unit 22 identifies the position of an area Zb(j) that is irradiated with radiation 30 that has not passed through the subject 34, based on the level of detected signals generated by the photodetectors 142 upon emission of light from the light-emitting device 136, and acquires the identified position as first coordinate information. An area within which the level of detected signals from the photodetectors 142 is equal to or higher than a threshold value may be judged as the area that is irradiated with radiation 30 that has not passed through the subject 34. Prior to a (j+1)th radiographic image capturing process, the second coordinate acquiring unit 128 identifies the position of an area Za(j+1) that is irradiated with radiation 30 that has passed through the subject 34, based on the level of detected signals generated by the photodetectors 142 upon emission of light from the light-emitting device 136, and acquires the identified position as second coordinate information. An area, which is produced by subtracting an area within which the level of detected signals from the photodetectors 142 is equal to or higher than a threshold value from the entire area defined by the profile of an area within which the level of detected signals from the photodetectors 142 is equal to or higher than a threshold value, may be judged as the area that is irradiated with radiation 30 that has passed through the subject 34. The timing information output unit 132 sends the timing of the (j+1)th radiographic image capturing process (radiographic image capturing process in its turn) as information concerning a predicted target timing to the console 28, if at least a portion of the area Za(j+1) represented by the second coordinate information is included within the area Zb(j) represented by the first coordinate information and, if necessary, that portion is included within the area Zd where the dose of radiation 30 is high.

In the following description, if at least a portion of the area Za(j+1) represented by the second coordinate information is included within the area Zb(j) represented by the first coordinate information and, if necessary, that portion is included within the area Zd where the dose of radiation 30 is high, then the portion is referred to as an "overlapping portion Zc" (see FIG. 8).

Prior to carrying out a radiographic image capturing process, which is to be executed at a predicted target timing, the console 28 controls the moving unit 20 in order to move the radiation detecting device 14. More specifically, the console 28 controls the moving unit 20 to move the radiation detecting device 14 in a direction that reduces the area of the overlapping portion Zc. The console 28 may control the moving unit 20 to move the radiation detecting device 14 for displacing the area Za(j+1), which is represented by the second coordinate information, out of the area Zb(j), which is represented by the first coordinate information. If the direction along the irradiated surface of the radiation detecting device 14 is defined as a horizontal direction (first direction), whereas the direction normal to the irradiated surface is defined as a vertical direction (second direction), then the moving unit 20 translates the radiation detecting device 14 in the horizontal direction or rotates the radiation detecting device 14 about the vertical direction, or translates the radiation detecting device 14 in the horizontal direction and rotates the radiation detecting device 14 about the vertical direction.

Figure 10:
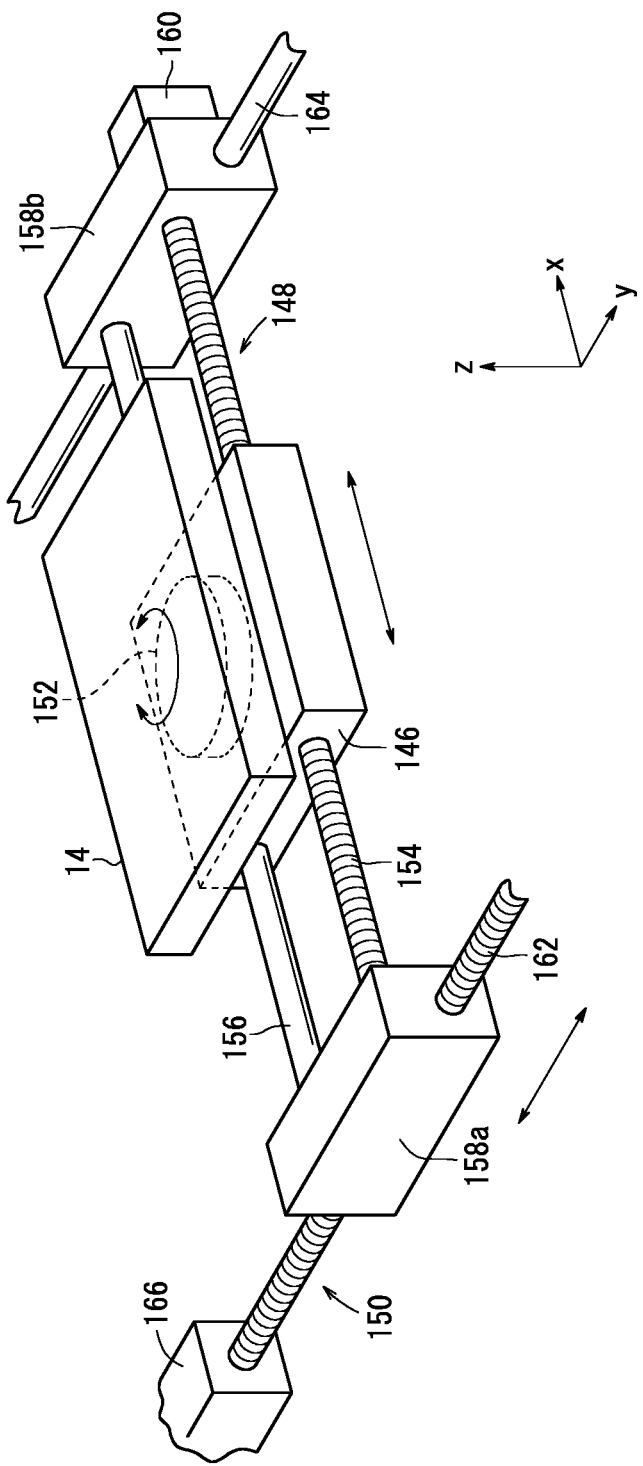
FIG. 10 is a perspective view showing by way of example specific mechanisms of a moving unit that moves the radiation detecting device.

An example of the structure of the moving unit 20, for moving the radiation detecting device 14 in the foregoing manner, is shown in FIG. 10. The moving unit 20 comprises a table 146 on which the radiation detecting device 14 is fixedly mounted, a first moving mechanism 148 for moving the table 146 in the x direction as a horizontal direction, a second moving mechanism 150 for moving the table 146 together with the first moving mechanism 148 in the y direction, and a rotating mechanism 152 (motor), which is mounted on the table 146, for rotating the radiation detecting device 14 about a vertical direction (z direction).

As shown in FIG. 10, the first moving mechanism 148 comprises a first feed screw 154 and a first guide pole 156 that extend through the table 146, a pair of supports 158a, 158b by which the first feed screw 154 is rotatably supported, and a first servomotor 160 for rotating the first feed screw 154 about its axis in order to move the table 146 in the x direction. The second moving mechanism 150 comprises a second feed screw 162 that extends through one of the supports 158a, a second guide pole 164 that extends through the other support 158b, and a second servomotor 166 for rotating the second feed screw 162 about its axis in order to move the table 146 together with the first moving mechanism 148 in the y direction. Of course, other structures may be used for moving the table 146 in biaxial directions.

If the radiation detecting device 14 is moved in synchronism with the radiation source 12, as shown in FIG. 5A, then the first moving mechanism 148 (or the second moving mechanism 150), for example, may double as a mechanism for moving the radiation source 12. Although in the above example the moving unit 20 is made up of the first moving mechanism 148, the second moving mechanism 150, and the rotating mechanism 152, the moving unit 20 may comprise only one of the first moving mechanism 148, the second moving mechanism 150, or the rotating mechanism 152. Alternatively, the moving unit 20 may be made up from the first moving mechanism 148 and the second moving mechanism 150, the first moving mechanism 148 and the rotating mechanism 152, or the second moving mechanism 150 and the rotating mechanism 152.

The image correction unit 24 shown in FIG. 1 corrects the radiographic image information, which was obtained by the radiographic image capturing process carried out at the target timing predicted by the timing prediction unit 22, from among the plural items of radiographic image information stored in the image memory 18, based on information concerning the movement made by the moving unit 20.

The image reconstructor 26 processes the radiographic images stored in the image memory 18 in order to generate or reconstruct a tomographic image of the subject 34, and in particular a tomographic image of a region of interest of the subject 34, which is oriented parallel to the detecting surface of the radiation detecting device 14. The reconstructing process may be a simple backprojection process or a filter backprojection process. Simple backprojection refers to a process of backprojecting a plurality of radiographic images without processing the radiographic images with a reconstruction filter, and then adding the backprojected radiographic images in order to obtain a reconstructed image. Filter backprojection refers to a process of processing a plurality of radiographic images with a convoluting filter, which serves as a reconstruction filter, and then backprojecting the radiographic images and adding the backprojected radiographic images in order to obtain a reconstructed image. Alternatively, filter backprojection may refer to a process of Fourier-transforming a plurality of radiographic images so as to convert the radiographic images into data in a frequency domain, processing the data with a reconstructing filter, backprojecting the data, and adding the backprojected data in order to obtain a reconstructed image. Either of these aforementioned processes may be used as a filter backprojection process.

Operations of the radiographic image capturing system 10, which includes the timing prediction unit 22 for carrying out the third method, will be described below with reference to FIGS. 11 through 14. According to the third method, as described above, a provisional image capturing process and a subsequent main image capturing process are combined to make up one radiographic image capturing process.

Figure 11:
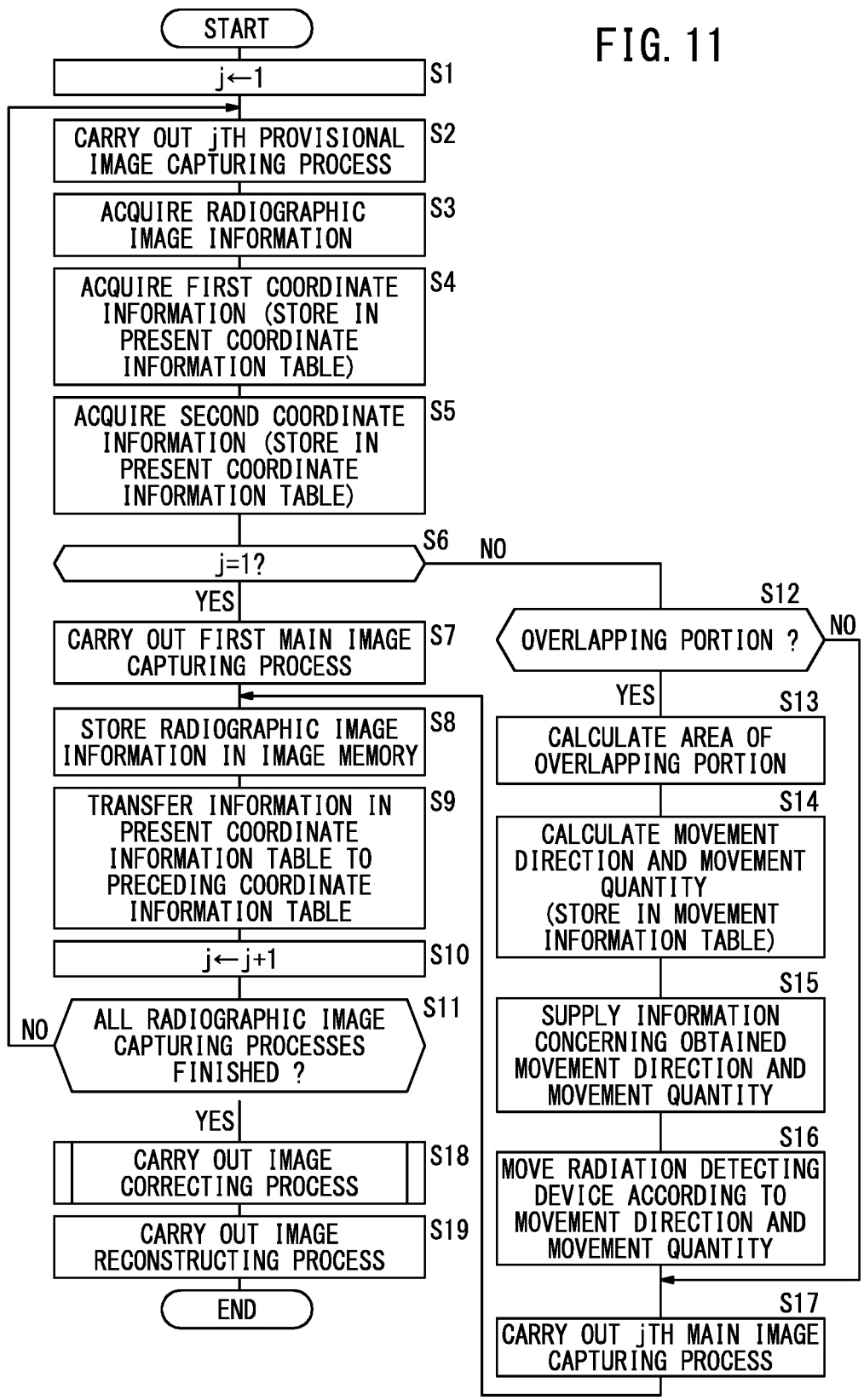
FIG. 11 is a flowchart of a processing sequence of the radiographic image capturing system.

In step S1 of FIG. 11, the value of a counter j, which indicates the number of radiographic image capturing processes, is set to an initial value of "1".

In step S2, the console 28 energizes the radiographic image acquiring unit 16, the radiation detecting device 14, etc., so as to perform a provisional image capturing process (hereinafter referred to as a "jth" process) in turn, as indicated by the value of the counter j.

In step S3, the timing prediction unit 22 acquires radiographic image information obtained by the provisional image capturing process.

In step S4, the first coordinate acquiring unit 126 of the timing prediction unit 22 stores an area $Zb(j)$, which has been irradiated with radiation 30 that has not passed through the subject 34 and is represented by the presently acquired radiographic image information, as first coordinate information in a present coordinate information table 168 (see FIG. 12A).

Similarly, in step S5, the second coordinate acquiring unit 128 stores an area $Za(j)$, which has been irradiated with radiation 30 that has passed through the subject 34 and is represented by the presently acquired radiographic image information, as second coordinate information in the present coordinate information table 168. In FIG. 12A, the first coordinate information and the second coordinate information are indicated as $Zb(j+1)$ and $Za(j+1)$, respectively, as will be described later.

In step S6, the timing prediction unit 22 judges whether or not the provisional image capturing process is a first provisional image capturing process, based on whether the value of the counter j is 1 or not. If the provisional image capturing process is a first provisional image capturing process, then control proceeds to step S7, in which the console 28 energizes the radiographic image acquiring unit 16, the radiation detecting device 14, etc., in order to carry out a first main image capturing process.

In step S8, the image storage unit 124 of the radiographic image acquiring unit 16 stores radiographic image information, which is obtained in turn by the first main image capturing process, in the image memory 18.

In step S9, the timing prediction unit 22 transfers the information stored in the present coordinate information table 168 to a preceding coordinate information table 170 (see FIG. 12B). At this time, the preceding coordinate information table 170 stores the area $Zb(j)$ as first coordinate information and the area $Za(j)$ as second coordinate information. In a repeated cycle carried out in step S4 and step S5, based on the first coordinate information and the second coordinate information stored in the preceding coordinate information table 170, the present coordinate information table 168 stores as first coordinate information an area $Zb(j+1)$, which has been irradiated with radiation 30 that has not passed through the subject 34, and stores as second coordinate information an area $Za(j+1)$, which has been irradiated with radiation 30 that has passed through the subject 34.

In step S10, the value of the counter j is incremented by +1.

In step S11, the timing prediction unit 22 judges whether or not all of the radiographic image capturing processes have been completed, based on whether the value of the counter j has exceeded a present image capturing count N or not. If all of the radiographic image capturing processes have not been completed, control returns to step S2, and the processes from step S2 onward are repeated.

If the timing prediction unit 22 judges that the provisional image capturing process is not a first provisional image capturing process, but rather is a second or subsequent provisional image capturing process, then control proceeds to step S12. In step S12, the area determiner 130 determines whether or not at least a portion of the area $Za(j+1)$ represented by the second coordinate information, which is stored in the present coordinate information table 168, overlaps with the area $Zb(j)$ represented by the first coordinate information, which is stored in the preceding coordinate information table 170. If there is an overlapping portion Zc, then control proceeds to step S13 in which the movement information generator 134 calculates the area of the overlapping portion Zc.

In step S14, the movement information generator 134 calculates a movement direction and a movement quantity, i.e., a direction and quantity at which the radiation detecting device 14 should be moved in order to reduce the area of the overlapping portion Zc, and records the calculated result as well as the value of the counter j in a movement information table 172

(see FIG. 12C). The movement information table 172 contains a plurality of records, each of which, with the exception of the final record, records in turn the movement direction and movement quantity calculated by the movement information generator 134, as well as the value of the counter j. The final record stores an EOF code representing the final record.

A movement direction and a movement quantity may be calculated in the following manner by the movement information generator 134.

The movement direction may be set as a direction in which the overlapping portion Zc is brought, partially or wholly, into the area Za(j) represented by the second coordinate information in the preceding coordinate information table 170, or a direction (straight or rotational direction) in which the overlapping portion Zc is brought, partially or wholly, into an area that has not been irradiated with radiation 30 in the preceding radiographic image capturing process. The area that has not been irradiated with radiation 30 refers to an area produced by subtracting both the area Zb(j), which is represented by the first coordinate information stored in the preceding coordinate information table 170, and the area Za(j), which is represented by the second coordinate information stored in the preceding coordinate information table 170, from among the entire area (image capturing area) of the converter 35.

Figure 13:
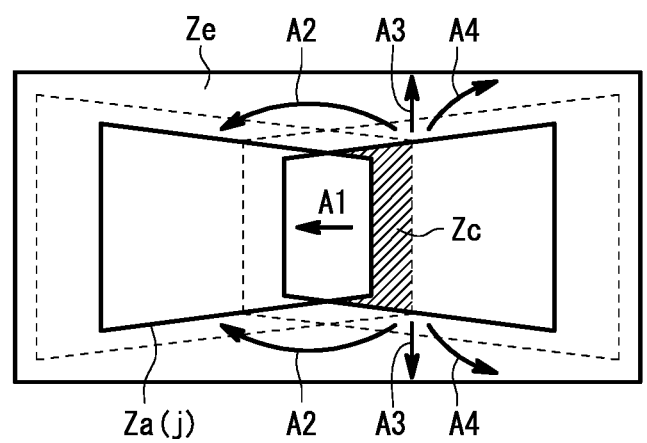
FIG. 13 is a diagram showing a manner in which overlapping radiation-irradiated areas are moved relative to each other.

For example, as shown in FIG. 13, if it is assumed that the overlapping portion is denoted by Zc, the area represented by the preceding second coordinate information (the area that was irradiated with radiation that has passed through the subject in the preceding radiographic image capturing process) is denoted by Za(j), and the area that has not been irradiated with radiation in the preceding radiographic image capturing process is denoted by Ze, then the movement direction may be set in the following manner.

(a) As indicated by the arrow A1, the radiation detecting device 14 is translated (moved straight) in order to translate (move straight) the overlapping portion Zc toward the area Za(j).

(b) As indicated by the arrows A2, the radiation detecting device 14 is rotated in order to rotate the overlapping portion Zc toward the area Za(j).

(c) As indicated by the arrows A3, the radiation detecting device 14 is translated in order to translate (move straight) the overlapping portion Zc toward the area Ze.

(d) As indicated by the arrows A4, the radiation detecting device 14 is rotated in order to rotate the overlapping portion Zc toward the area Ze.

The movement quantity is calculated by presetting quantities (linear distances and rotational angles) such as 0.5 cm, 1 cm, 1.5 cm, 2 cm, ..., 10 cm for the aforementioned straight directions and 5°, 10°, 15°, ..., 180° for the aforementioned rotational directions, and selecting from the preset quantities a quantity that minimizes the area of the overlapping portion. Of course, a plurality of computational formulas, which are based on combinations of linear distances and rotational angles, may be made available, and one of such computational formulas can be selected in order to minimize the area of the overlapping portion.

In step S15, the timing information output unit 132 supplies information concerning the present movement direction and the present movement quantity, which is obtained in step S14, to the console 28 together with the value of the counter j.

In step S16, the console 28 controls the moving unit 20 in order to move the radiation detecting device 14 according to the movement direction and quantity obtained from the timing information output unit 132.

In step S17, the console 28 energizes the radiographic image acquiring unit 16, the radiation detecting device 14, etc., in order to perform a jth main image capturing process.

After the process of step S17 is completed, control proceeds to step S8, and the process of step S8 is carried out.

If the timing prediction unit 22 judges that all of the radiographic image capturing processes have been completed in step S11, then control proceeds to step S18 in which the processing sequence of the image correction unit 24 is performed.

Figure 14:
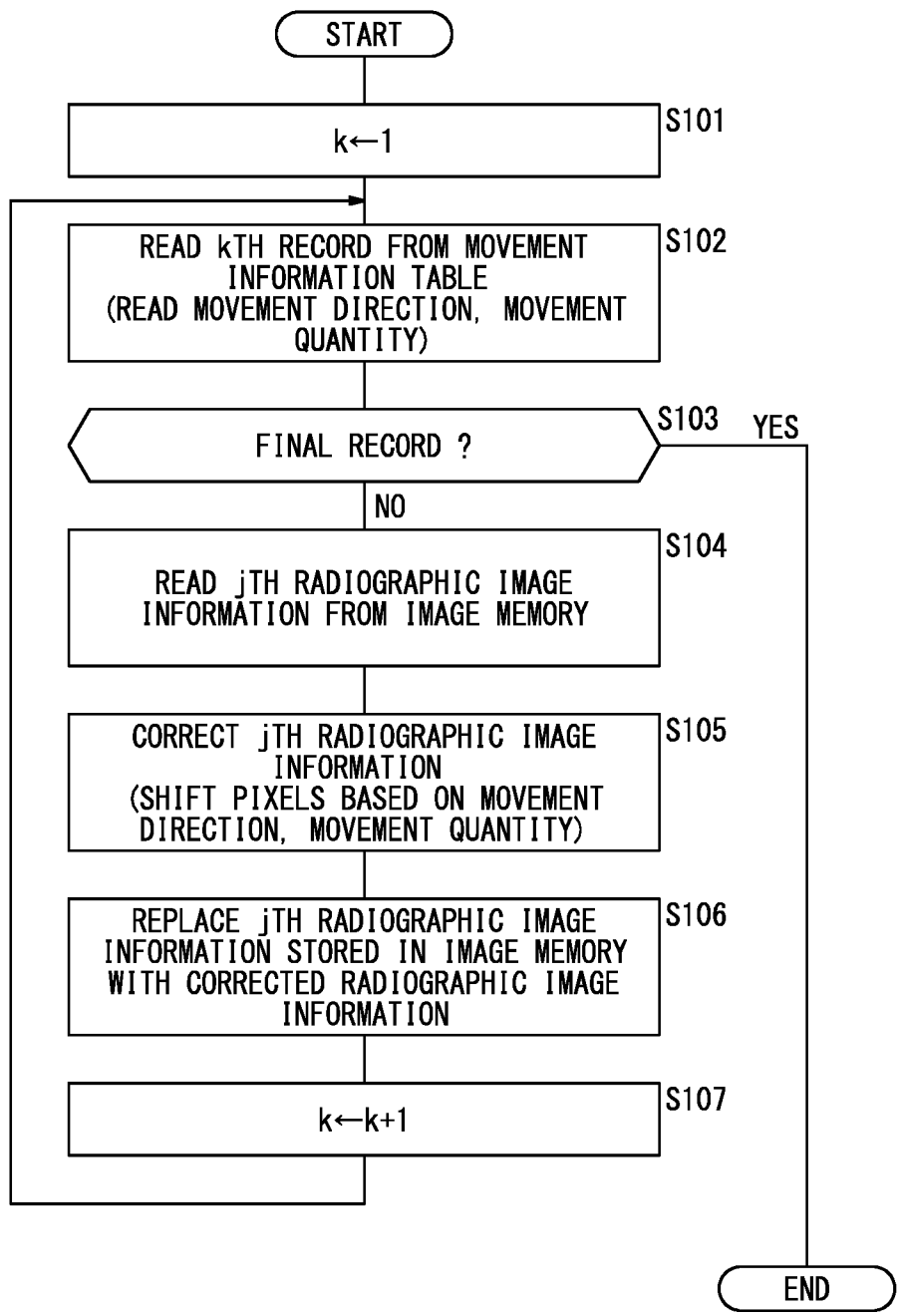
FIG. 14 is a flowchart of a processing sequence of an image correction unit.

A processing sequence of the image correction unit 24 will be described below with reference to the flowchart shown in FIG. 14.

In step S101, the value of a counter k, which is used to access respective records in the movement information table 172 (see FIG. 12C), is set to an initial value of "1".

In step S102, the image correction unit 24 reads the data of the record (kth record) in the movement information table 172, which is represented by the value of the counter k.

In step S103, the image correction unit 24 judges whether or not the kth record is the final record, based on whether the kth record in an EOF code. If the kth record is not the final record, then control proceeds to step S104 in which the image correction unit 24 reads the value of the counter j from the kth record, and also reads the jth radiographic image information stored in the image memory 18.

In step S105, the image correction unit 24 corrects (shifts the pixel data of) the jth radiographic image information. More specifically, the image correction unit 24 reads information concerning the direction and quantity from the kth record, and shifts the pixel data of the jth radiographic image information based on the read information, so as to bring the origin of the jth radiographic image information into conformity with the origin of the other radiographic image information (the radiographic image information acquired in a case where the radiation detecting device 14 was not moved).

In step S106, the image correction unit 24 replaces the jth radiographic image information recorded in the image memory 18 with the corrected jth radiographic image information.

In step S107, the value of the counter k is incremented by +1. Thereafter, control returns to step S102, and the processes from step S102 onward are repeated.

If the image correction unit 24 judges that the kth record is a final record in step S103, then the processing sequence of the image correction unit 24 is brought to an end.

Referring back to the main routine shown in FIG. 11, the image reconstructor 26 performs the processing sequence thereof in step S19 in order to process the radiographic images that are stored in the image memory 18, thereby reconstructing a tomographic image of the subject 34, and in particular a tomographic image of a region of interest of the subject 34, which is oriented parallel to the detecting surface of the radiation detecting device 14.

Upon completion of the process in step S19, the processing sequence of the radiographic image capturing system 10 is brought to an end.

Operations of the radiographic image capturing system 10, which includes the timing prediction unit 22 used in carrying out the fourth method, will be described below. According to the fourth method, as described above, and as shown in FIGS. 9A and 9B, in contrast to the provisional image capturing process carried out in the third method, light 138 from a light-emitting device 136 is applied to the subject 34, and the light 138 is detected by the photodetectors 142 disposed behind the subject 34.

The radiographic image capturing system 10 operates similarly to the radiographic image capturing system 10 according to the third method, except that steps S2 through S5 shown in FIG. 11 differ as described below.

In step S2, the console 28 controls the light-emitting device 136 in order to emit light 138 prior to the jth radiographic image capturing process.

In step S3 and step S4, the first coordinate acquiring unit 126 identifies the position of an area Zb(j), which is irradiated with radiation 30 that has not passed through the subject 34, based on the level of detected signals generated by the photodetectors 142 upon emission of light from the light-emitting device 136. The first coordinate acquiring unit 126 stores the identified area Zb(j) as second coordinate information in the present coordinate information table 168.

In step S5, the second coordinate acquiring unit 128 identifies the position of an area Za(j), which is irradiated with radiation 30 that has passed through the subject 34, based on the level of detected signals from the photodetectors 142. The second coordinate acquiring unit 128 stores the identified position of the area Za(j) as first coordinate information in the present coordinate information table 168.

As described above, the radiographic image capturing system 10 according to the present embodiment predicts a target timing at which an area Zb(j) is irradiated with radiation 30 that has not passed through the subject 34 in the jth radiographic image capturing process, and with radiation 30 that has passed through the subject 34 in the (j+1)th radiographic image capturing process. Further, the radiographic image capturing system 10 actuates the moving unit 20 in order to move the radiation detecting device 14 prior to a radiographic image capturing process that is carried out at the predicted target timing. Therefore, it is possible to capture an image while avoiding regions in which afterimage phenomena tend to occur. In other words, with a simple arrangement, it is possible to capture an image while avoiding regions in which afterimage phenomena occur, independently of the outer profile of the subject 34. In addition, the radiographic image capturing system 10 is capable of preventing the S/N ratio and contrast from being lowered, and the radiographic image capturing system 10 can be produced at a reduced cost without lowering the degree of freedom in designing the radiation detecting device. According to the present embodiment, furthermore, the radiographic image capturing system 10 can be applied easily to a tomosynthetic image capturing process, for example, for capturing a hundred or more radiographic images within a short period of time, thereby making it possible to increase the image quality of a reconstructed tomographic image of the subject 34.

The timing prediction unit 22 may employ the first method or the second method described above in order to determine a target timing by collectively processing a plurality of items of radiographic image information, which are obtained by way of simulation, or a plurality of items of radiographic image information acquired from history information. In this manner, it is possible to obtain the target timing before a tomosynthetic image capturing process actually is carried out on the subject 34, thereby resulting in a reduced image processing burden for each of the radiographic image capturing process compared with the third method and the fourth method. Furthermore, unlike the third method (a provisional image capturing process and a main image capturing process), the exposure dose applied to the subject 34 is not increased.

The timing prediction unit 22 may employ the third method or the fourth method described above in order to determine a target timing according to a real-time process, so that movements of the body of the subject 34 can flexibly be dealt with, an overlapping portion can be grasped, and a direction in which the radiation detecting device 14 is moved can be selected appropriately. Although the third method requires a provisional image capturing process and a main image capturing process, both of which are carried out in one radiographic image capturing process, the third method does not require installation of the light-emitting device 136 and the photodetectors 142. Further, the third method can be carried out with the existing structure, and hence is low in cost compared with the fourth method. The fourth method does not increase the exposure dose applied to the subject 34, although the fourth method requires the light-emitting device 136 and the photodetectors 142 to be installed.

According to the present embodiment, the moving unit 20, which moves the radiation detecting device 14, may comprise an existing type of biaxial table, a motor, etc., which have proven effective as mechanisms for moving the radiation detecting device 14 at the target timing.

Among the items of radiographic image information that are stored in the image memory 18, the radiographic image information, which is obtained by the radiographic image capturing process carried out at the target timing, is corrected based on information concerning movements made by the moving unit 20. Therefore, the origins of all of the items of radiographic image information stored in the image memory 18 can be brought into alignment with each other, and a simple backprojection process or a filter backprojection process, which are known in the art, may be used as a reconstruction process to be carried out subsequently by the image reconstructor 26.

In the above embodiment, the moving unit 20 moves the radiation detecting device 14. However, only the converter 35 in the radiation detecting device 14 may be moved.

A structure (modification), which enables movement of only the converter 35 in the radiation detecting device 14, will be described below with reference to FIGS. 15 and 16.

Figure 15:
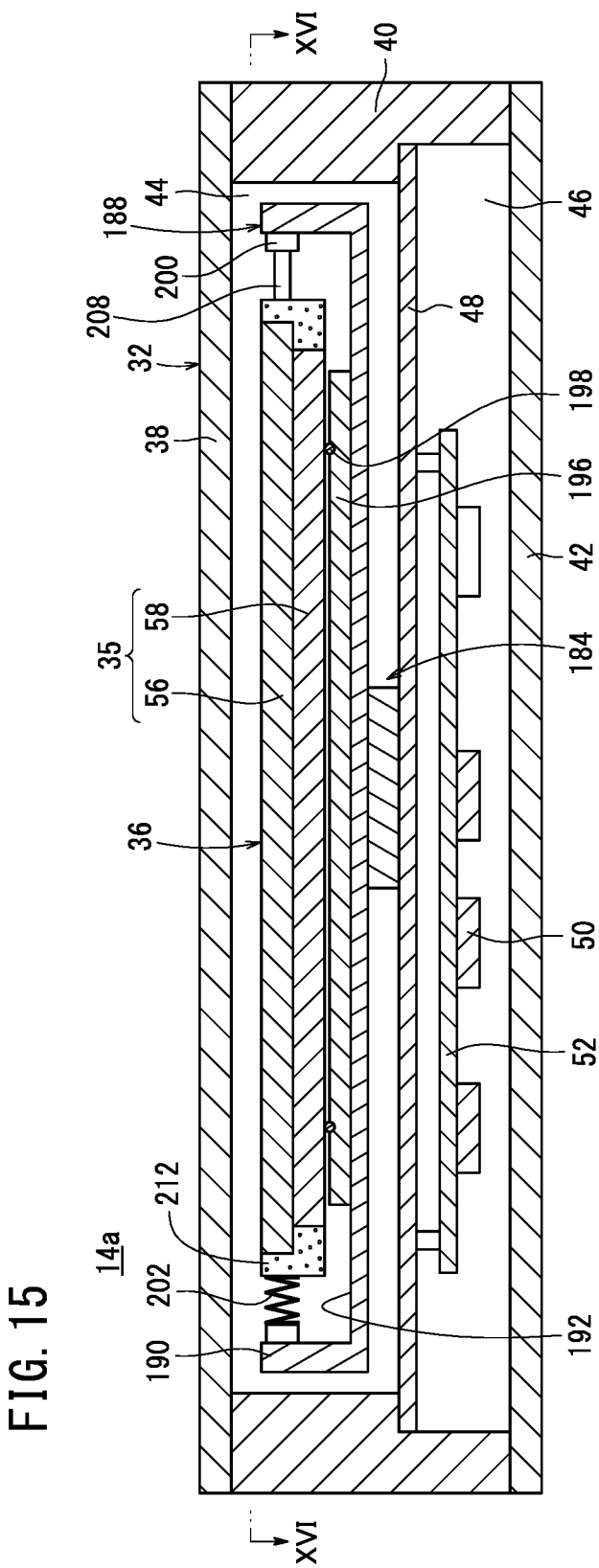
FIG. 15 is a vertical cross-sectional view of a radiation detecting device according to a modification in which the converter is movable.
Figure 16:
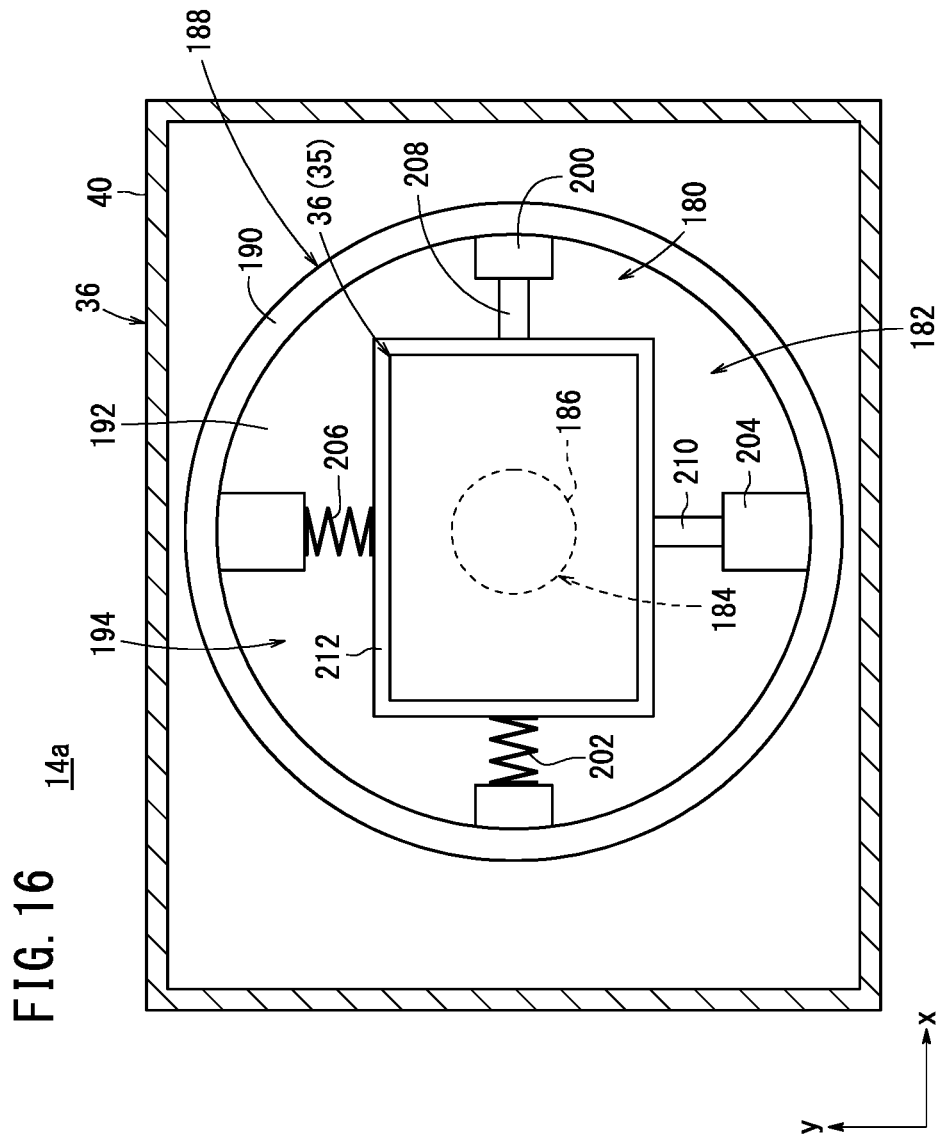
FIG. 16 is a cross-sectional view taken along line XVI-XVI of FIG. 15.

As shown in FIG. 15, similar to the case of the above-described radiation detecting device 14, a radiation detecting device 14a according to a modification includes a casing 32, a front plate 38, a frame 40, a rear plate 42, a first compartment 44, a second compartment 46, a partition 48, a circuit board 52, and a radiation detector 36.

The radiation detecting device 14a according to the modification further includes a first moving mechanism 180 for moving the converter 35 of the radiation detector 36 in the x direction, a second moving mechanism 182 for moving the converter 35 in the y direction, and a rotating mechanism 184 for rotating the converter 35 about a vertical direction (z direction).

The rotating mechanism 184 comprises a motor 186, which is fixedly mounted on a surface of the partition 48 that faces toward the first compartment 44, and a circular rotary table 188 that is rotatable by the motor 186. The rotary table 188 includes an annular side wall 190 extending upwardly from an outer circumferential edge thereof. The side wall 190 is either integral with or separate from the rotary table 188. The radiation detector 36 is housed in a housing space 194, which is defined by an upper surface 192 of the rotary table 188 and an inner surface of the side wall 190. As shown in FIG. 15, a slide support plate 196 for slidingly supporting the radiation detector 36 is mounted on the upper surface 192 of the rotary table 188. A plurality of small balls 198 are rotatably disposed on the upper surface of the slide support plate 196, thereby slidably supporting the radiation detector 36, which is placed on the upper surface of the slide support plate 196.

The first moving mechanism 180 includes a first actuator 200 mounted on the inner surface of the side wall 190 of the rotary table 188 in confronting relation to one side (along the y direction) of the converter 35, and a first resilient member 202 (compression spring or the like) disposed opposite to the first actuator 200.

The second moving mechanism 182 includes a second actuator 204 mounted on the inner surface of the side wall 190 of the rotary table 188 in confronting relation to one side (along the x direction) of the converter 35, and a second resilient member 206 (compression spring or the like) disposed opposite to the second actuator 204.

A protective frame 212 preferably is disposed on the outer circumferential edge of the converter 35. The protective frame 212 bears a tip end of a first plunger 208 of the first actuator 200, a tip end of a second plunger 210 of the second actuator 204, a tip end of the first resilient member 202, and a tip end of the second resilient member 206.

If the console 28 controls the moving unit 20 in order to displace the first plunger 208 of the first actuator 200, the converter 35 moves in the x direction. If the console 28 controls the moving unit 20 in order to displace the second plunger 210 of the second actuator 204, the converter 35 moves in the y direction. If the console 28 controls the moving unit 20 in order to energize the motor 186 of the rotating mechanism 184, the converter 35 is rotated.

In order for the console 28 to control the moving unit 20, the console 28 supplies control information concerning a direction and quantity by which the radiation detecting device 14 should be moved, through the transceiver 74 of the radiation detecting device 14 to the cassette controller 72, whereupon the cassette controller 72 supplies drive signals to the first actuator 200, the second actuator 204, and the motor 186.

Although, in the above example, the moving unit 20 is made up of the first moving mechanism 180, the second moving mechanism 182, and the rotating mechanism 184, the moving unit 20 may comprise only one of the first moving mechanism 180, the second moving mechanism 182, or the rotating mechanism 184. Alternatively, the moving unit 20 may be made up of the first moving mechanism 180 and the second moving mechanism 182, the moving unit 20 may be made up of the first moving mechanism 180 and the rotating mechanism 184, or the moving unit 20 may be made up of the second moving mechanism 182 and the rotating mechanism 184.

According to the above modification, since the converter 35 in the radiation detecting device 14 is moved by the moving unit 20, the moving unit 20 may be of a compact structure, thereby enabling the installation space for the radiographic image capturing system 10 to be reduced. Further, since only the converter 35 is moved, any adverse effects of inertial force may be smaller than if the radiation detecting device 14 were moved, and the time (response time) consumed after the console 28 issues a moving instruction and until the movement of the converter 35 is completed can be shortened.

The radiographic image capturing system according to the present invention is not limited to the above-described embodiments, but various arrangements may be adopted without departing from the scope of the invention.

The invention claimed is:

1. A radiographic image capturing system comprising:
   a radiation source;
   a radiation detecting device including a casing and a radiation detector housed in the casing, the radiation detector having a converter for converting radiation emitted from the radiation source that has passed through at least a subject into radiographic image information;
   a moving unit for moving at least the converter;
   a timing prediction unit for predicting a target timing at which to irradiate an area, which has been irradiated with radiation that has not passed through the subject in a preceding radiographic image capturing process, with radiation that passes through the subject in a next radiographic image capturing process; and
   a controller,
   wherein the controller controls the moving unit to move at least the converter prior to a radiographic image capturing process carried out at the predicted target timing.

2. The radiographic image capturing system according to claim 1, wherein a first direction is defined as a direction along an irradiated surface of the radiation detecting device, and a second direction is defined as a direction normal to the irradiated surface of the radiation detecting device; and
   the moving unit translates at least the converter in the first direction.

3. The radiographic image capturing system according to claim 1, wherein a first direction is defined as a direction along an irradiated surface of the radiation detecting device, and a second direction is defined as a direction normal to the irradiated surface of the radiation detecting device; and
   the moving unit rotates at least the converter about the second direction.

4. The radiographic image capturing system according to claim 1, wherein a first direction is defined as a direction along an irradiated surface of the radiation detecting device, and a second direction is defined as a direction normal to the irradiated surface of the radiation detecting device; and
   the moving unit translates at least the converter in the first direction and rotates at least the converter about the second direction.

5. The radiographic image capturing system according to claim 1, wherein the moving unit moves the radiation detecting device.

6. The radiographic image capturing system according to claim 1, wherein the moving unit moves only the converter in the radiation detecting device.

7. The radiographic image capturing system according to claim 1, further comprising:
   a second moving unit for moving the radiation source, which is disposed in confronting relation to the radiation detecting device, to a plurality of positions,
   wherein the controller controls the radiation source at the positions to apply radiation in different directions to the subject over the radiation detecting device.

8. The radiographic image capturing system according to claim 7, wherein the second moving unit moves only the radiation source.

9. The radiographic image capturing system according to claim 7, wherein the second moving unit moves the radiation source and the radiation detecting device synchronously in opposite directions while the subject is disposed between the radiation source and the radiation detecting device.

10. The radiographic image capturing system according to claim 7, wherein the timing prediction unit predicts the target timing at which to irradiate the area, which has been irradiated with the radiation that has not passed through the subject in the preceding radiographic image capturing process, with the radiation that passes through the subject in the next radiographic image capturing process at the positions.

11. The radiographic image capturing system according to claim 10, wherein the timing prediction unit predicts the target timing based on a simulation of the radiographic image capturing processes at the positions.

12. The radiographic image capturing system according to claim 10, wherein the timing prediction unit predicts the target timing based on history information of the radiographic image capturing processes at the positions.

13. The radiographic image capturing system according to claim 10, wherein the timing prediction unit predicts the target timing each time that the radiation source reaches one of the positions.

14. The radiographic image capturing system according to claim 1, wherein the timing prediction unit comprises:
   a first coordinate acquiring unit for acquiring first coordinate information representing the area that is irradiated with the radiation that has not passed through the subject in the preceding radiographic image capturing process;
   a second coordinate acquiring unit for acquiring second coordinate information representing an area that is irradiated with the radiation that passes through the subject in the next radiographic image capturing process; and
   a timing information output unit for sending a timing for carrying out the next radiographic image capturing process as the target timing to the controller, if the area represented by the first coordinate information and at least a portion of the area represented by the second coordinate information overlap with each other,
   wherein the controller actuates the moving unit prior to a radiographic image capturing process to be carried out at the predicted target timing, so as to move at least the converter in a direction to reduce the portion of the area represented by the second coordinate information that overlaps with the area represented by the first coordinate information.

15. The radiographic image capturing system according to claim 14, wherein one radiographic image capturing process comprises a provisional image capturing process and a main image capturing process subsequent thereto;
   the first coordinate acquiring unit acquires the first coordinate information representing the area that is irradiated with the radiation that has not passed through the subject, which is represented by radiographic image information obtained by a preceding provisional image capturing process; and
   the second coordinate acquiring unit acquires the second coordinate information representing the area that is irradiated with the radiation that passes through the subject, which is represented by radiographic image information obtained by a next provisional image capturing process.

16. The radiographic image capturing system according to claim 14, further comprising:
   a light-emitting device for emitting light toward the subject prior to each of the radiographic image capturing process; and
   a plurality of photodetectors disposed behind the subject, for detecting the light emitted from the light-emitting device;
   wherein the first coordinate acquiring unit identifies an area that is irradiated with the radiation that has not passed through the subject, based on detected signals obtained from the photodetectors prior to a preceding radiographic image capturing process, and acquires the identified area as the first coordinate information; and
   the second coordinate acquiring unit identifies an area that is irradiated with the radiation that passes through the subject, based on detected signals obtained from the photodetectors prior to a next radiographic image capturing process, and acquires the identified area as the second coordinate information.

17. The radiographic image capturing system according to claim 1 further comprising:
   an image correction unit for correcting the radiographic image information obtained by the radiographic image capturing process carried out at the target timing, based on information concerning movement of at least the converter performed by the moving unit.

* * * * *